US007379823B2

(12) United States Patent
Yung et al.

(10) Patent No.: US 7,379,823 B2
(45) Date of Patent: May 27, 2008

(54) SYSTEM AND METHOD FOR DISCOVERY OF BIOLOGICAL INSTRUMENTS

(75) Inventors: Kai Yung, Livermore, CA (US); Sylvia H. Fang, Fremont, CA (US); John Rohrlich, Niwot, CO (US); Stephen L. Dodgen, Stockton, CA (US)

(73) Assignee: Applera Corporation, Foster City, CA (US)

( * ) Notice: Subject to any disclaimer, the term of this patent is extended or adjusted under 35 U.S.C. 154(b) by 451 days.

(21) Appl. No.: 11/023,329

(22) Filed: Dec. 27, 2004

(65) Prior Publication Data

US 2005/0106736 A1 May 19, 2005

Related U.S. Application Data

(63) Continuation of application No. 10/455,264, filed on Jun. 4, 2003, now Pat. No. 6,909,974.

(60) Provisional application No. 60/411,574, filed on Sep. 16, 2002, provisional application No. 60/386,296, filed on Jun. 4, 2002.

(51) Int. Cl.
*G06F 19/00* (2006.01)

(52) U.S. Cl. ...................................... 702/19; 340/359.1

(58) Field of Classification Search .................. 702/19, 702/20, 23, 30, 32; 340/539.1, 3.1
See application file for complete search history.

(56) References Cited

U.S. PATENT DOCUMENTS 5,029,065 A 7/1991 Nau et al.
5,841,975 A 11/1998 Layne et al.
6,202,153 B1 * 3/2001 Diamant et al. .............. 726/35
6,507,945 B1 1/2003 Rust et al.
6,689,324 B2 2/2004 Inoue
6,727,096 B1 4/2004 Wang et al.
6,824,742 B1 11/2004 Inoue
6,909,974 B2 6/2005 Yung et al.
6,944,522 B2 9/2005 Karmiy et al.
6,983,227 B1 1/2006 Thalhammer-Reyero
6,990,221 B2 1/2006 Shams
2002/0013832 A1 1/2002 Hubbard (Continued)

FOREIGN PATENT DOCUMENTS

EP 0 596 205 8/1993

(Continued)

OTHER PUBLICATIONS

Amend to Correct Informalities filed Nov. 8, 2004, for U.S. Appl. No. 10/455,264.

(Continued)

*Primary Examiner*—Edward Raymond
(74) *Attorney, Agent, or Firm*—Knobbe, Martens, Olson & Bear, LLP

(57) ABSTRACT

A system and methods for integrating laboratory instrumentation and applications to provide a unified control and coordination architecture under a common interface. The system provides mechanisms for detection of various hardware and software components wherein the individual functionalities and input/output data types for each component are automatically recognized and incorporated into a centralized control system that provides live monitoring of the operational status of available components.

39 Claims, 23 Drawing Sheets

U.S. PATENT DOCUMENTS

| | | | |
|---|---|---|---|
| 2003/0055835 | A1 | 3/2003 | Roth |
| 2004/0012633 | A1 | 1/2004 | Helt |
| 2004/0030504 | A1 | 2/2004 | Helt et al. |
| 2004/0032430 | A1 | 2/2004 | Yung et al. |
| 2004/0034478 | A1 | 2/2004 | Yung et al. |
| 2004/0039531 | A1 | 2/2004 | Yung et al. |
| 2004/0042471 | A1 | 3/2004 | Yung et al. |
| 2005/0106736 | A1 | 5/2005 | Yung |
| 2007/0129894 | A1 | 6/2007 | Yung et al. |

FOREIGN PATENT DOCUMENTS

| | | |
|---|---|---|
| WO | WO99/27427 | 11/1998 |
| WO | WO 01/59406 | 8/2001 |
| WO | WO 01/90951 | 11/2001 |

OTHER PUBLICATIONS

Amend After Notice of Allowance filed Oct. 7, 2004 for U.S. Appl. No. 10/455,264.

Notice of Allowance of Sep. 3, 2004 for U.S. Appl. No. 10/455,264.

RCE and IDS in response to NOA of Oct. 18, 2007 for U.S. Appl. No. 10/455,262.

Supplemental Notice of Allowance of Oct. 18, 2007 for U.S. Appl. No. 10/455,262.

Notice of Allowance of Aug. 14, 2007 for U.S. Appl. No. 10/455,262.

Terminal Disclaimer and Response to Office Action of Apr. 10, 2007 for U.S. Appl. No. 10/455,262.

Office Action of Apr. 10, 2007 for U.S. Appl. No. 10/455,262.

Preliminary Amendment of Feb. 11, 2005 for U.S. Appl. No. 10/455,262

Office Action of Sep. 12, 2007 for U.S. Appl. No. 10/455,263.

RCE and Response to Final Office Action of Apr. 10, 2007 for U.S. Appl. No. 10/455,263.

Advisory Action of Jun. 21, 2007 for U.S. Appl. No. 10/455,263.

Response to Final Office Action of Apr. 10, 2007 for U.S. Appl. No. 10/455,263.

Final Office Action of Apr. 10, 2007 for U.S. Appl. No. 10,455,263.

Response to Office Action of Oct. 11, 2006 for U.S. Appl. No. 10/455,263.

Office Action of Oct. 11, 2006 for U.S. Appl. No. 10/455,263.

Preliminary Amendment filed Feb. 11, 2005 for U.S. Appl. No. 10/455,263.

Office Action of Sep. 21, 2007 for U.S. Appl. No. 10/454,759.

RCE and Office Action Response of Apr. 5, 2007 for U.S. Appl. No. 10/454,759.

Final Office Action of Apr. 5, 2007 for U.S. Appl. No. 10/454,759.

Terminal Disclaimer and Office Action Response of Oct. 4, 2006 for U.S. Appl. No. 10/454,759.

Office Action of Oct. 4, 2006 for U.S. Appl. No. 10/454,759.

Preliminary Amendment filed Feb. 11, 2005 for U.S. Appl. No. 10/454,759.

International Search Report for PCT/US2003/017940.

* cited by examiner

FIG. 11

| | Function call | Behavior |
|---|---|---|
| 1105 | GetInstState() | Queries the instrument driver for its current state. |
| 1110 | GetInstStatus() | Queries the instrument driver for its status data. |
| 1115 | InitializeInstrument() | Instructs instrument driver to initialize. |
| 1120 | ManualControlCommand(<command>) | Sends a manual control command to instrument. |
| 1125 | Pause() | Instructs the service provider to stay at its current state and instructs the instrument to pause. |
| 1130 | PerformSelfDiagnostics() | Instructs the instrument to perform self diagnostic. |
| 1135 | Resume() | Instructs the instrument to resume its previous state. |
| 1140 | ShutDown() | Instructs the instrument driver to put the instrument in a safe place and power off instrument if possible. |
| 1145 | StartBatch() | Instructs instrument to start a batch run. |
| 1150 | StopAfterCurrentRun() | Instructs instrument to stop after the current run. |
| 1155 | StopImmediately() | Instructs instrument to stop immediately regardless the state of current run. |

FIG. 12A

Container and Assay Parameters Example

```
  - <ICFContainerParameters>
    - <ContainerNameColumn>
        <ColumnDisplayName>Container Name</ColumnDisplayName>
        </ContainerNameColumn>
    - <ContainerIDColumn>
        <ColumnDisplayName>Container Barcode ID</ColumnDisplayName>
1210  </ContainerIDColumn>
    - <ContainerOwnerColumn>
        <ColumnDisplayName>Owner</ColumnDisplayName>
      </ContainerOwnerColumn>
    - <CommentColumn>
        <ColumnDisplayName>Comment</ColumnDisplayName>
      </CommentColumn>
    - <ContainerInfoEntry>
        <KeyString>PLATE_TYPE</KeyString>
1215    <DisplayName>Plate Type</DisplayName>
        <isInputRequired>true</isInputRequired>
      - <ValueType>
        - <List>
          - <ListItem>
              <DisplayString>96 Well Plate</DisplayString>
              <ValueString>96_WELL</ValueString>
            </ListItem>
1220      - <ListItem>
              <DisplayString>384 Well Plate</DisplayString>
              <ValueString>384_WELL</ValueString>
            </ListItem>
          </List>
        </ValueType>
      </ContainerInfoEntry>
    - <ContainerInfoEntry>
        <KeyString>ASSAY_TEMPLATE</KeyString>
        <DisplayName>Assay Template</DisplayName>
        <isInputRequired>true</isInputRequired>
      - <ValueType>
1225    - <Dynamic>
            <ClassName>com.apldbio.udc.ICFImp.GetAssayType</ClassName>
          </Dynamic>
        </ValueType>
      </ContainerInfoEntry>
    + <ContainerInfoEntry>
    - <ContainerInfoEntry>
        <KeyString>PLATE_SEAL</KeyString>
        <DisplayName>Plate Sealing</DisplayName>
        <isInputRequired>true</isInputRequired>
      - <ValueType>
1230    - <List>
          - <ListItem>
```

FIG. 12B

```
            <DisplayString>Septa</DisplayString>
            <ValueString>SEPTA</ValueString>
          </ListItem>
        - <ListItem>
            <DisplayString>Heat Seal</DisplayString>
            <ValueString>HEAT SEAL</ValueString>
          </ListItem>
        </List>
      </ValueType>
    </ContainerInfoEntry>
  - <ContainerInfoEntry>
      <KeyString>SCHEDULE_PREF</KeyString>
      <DisplayName>Scheduling Preference</DisplayName>
      <isInputRequired>true</isInputRequired>
    - <ValueType>
      - <Integer>
          <MinValue>0123</MinValue>
          <MaxValue>3210</MaxValue>
        </Integer>
      </ValueType>
    </ContainerInfoEntry>
  </ICFContainerParameters>
```

Container Example

```
- <ICFContainer>
      <ContainerName>GM Plate 1</ContainerName>
      <ContainerID>AB154234</ContainerID>
1305  <Owner>Kai Yung</Owner>
      <Comment>This is a demo plate to demonstrate the input format for a
              IS container</Comment>
      <PlateType>96-Well</PlateType>
  - <ContainerAttribute>
1310    <Key>PlateSealing</Key>
        <Value>Heat Seal</Value>
    </ContainerAttribute>
  - <ContainerAttribute>
1315    <Key>SchedulingPref</Key>
        <Value>01234</Value>
    </ContainerAttribute>
  - <AssayData>
      <AssayTemplate>GM GenoTyping</AssayTemplate>
      <AssayInstance>Kai Laptop 1</AssayInstance>
    - <SampleData>
        <Name>Sample 1</Name>
        <TrackingID>123456</TrackingID>
        <WellName>Al</WellName>
        <Comment>This is sample 1</Comment>
      - <SampleAttribute>
          <Key>ResultsGroup</Key>
1320      <Value>DefaultResultsGroup</Value>
        </SampleAttribute>
      - <SampleAttribute>
          <Key>InstrumentProtocol</Key>
          <Value>3730xlProtocoll</Value>
        </SampleAttribute>
      </SampleData>
    - <SampleData>
        <Name>Sample 2</Name>
        <TrackingID>123457</TrackingID>
        <WellName>A2</WellName>
        <Comment>This is sample 2</Comment>
      - <SampleAttribute>
          <Key>ResultsGroup</Key>
          <Value>DefaultResultsGroup</Value>
        </SampleAttribute>
      - <SampleAttribute>
          <Key>InstrumentProtocol</Key>
          <Value>3730xlProtocol3</Value>
        </SampleAttribute>
      </SampleData>
    </AssayData>
</ICFContainer>
```

FIG. 14

Manual Control Parameters Example

```
- </manual-control-commands>
   + <group>
   - <group>
1405    <name>Electrophoresis</name>
      + <command>
      - <command>
1410       <name>Set electrophoresis power supply</name>
1415       <exec-string>EPS #</exec-string>
1420       <comment>Turns the power supply on or off. Capillary ends
                   should be in buffer.</comment>
           <visible>true</visible>
1425     - <param>
              <classification>LIST</classification>
              <default>On</default>
            - <range>
              - <value-list>
                   <value>On</value>
                   <value>Off</value>
                </value-list>
              </range>
           </param>
        </command>
1445  - <command>
          <name>Set electrophoresis voltage</name>
          <exec-string>EPS:VOLT:SETT #</exec-string>
          <comment>Sets voltage from 0 to 15kV. Capillary ends should be
                  in buffer.</comment>
          <visible>true</visible>
        - <param>
             <classification>FLOAT</classification>
             <default>1.0</default>
           - <range>
                <min>0.0</min>
                <max>15.0</max>
                <unit>kV</unit>
             </range>
          </param>
       </command>
     - <command>
1460     <name>Read electrophoresis voltage</name>
         <exec-string>EPS:VOLT:READ?</exec-string>
         <comment>Reads the present power supply setting.</comment>
         <visible>true</visible>
       </command>
    </group>
  </manual-control-commands>
```

SYSTEM AND METHOD FOR DISCOVERY OF BIOLOGICAL INSTRUMENTS

CLAIM OF PRIORITY

This application is a continuation of U.S. patent application Ser. No. 10/455,264 entitled "System and Method for Discovery of Biological Instruments" filed Jun. 4, 2003 now U.S. Pat. No. 6,909,974. This U.S. patent application claims priority to U.S. Provisional Patent Application No. 60/386,296 entitled "Informatics System Architecture" filed Jun. 4, 2002 and U.S. Provisional Patent Application No. 60/411,574 entitled "Integration Instructions For Informatics System Architecture" filed Sep. 16, 2002 which are hereby incorporated by reference. Additionally, this application relates to the following co-pending applications filed on the same date which are hereby incorporated by reference in their entirety: entitled "System And Method For Open Control And Monitoring Of Biological Instruments", entitled "System And Method For Providing A Standardized State Interface For Instrumentation", and entitled "System And Method For Generating User Interfaces For Different Instrument Types".

BACKGROUND

1. Field

The present invention relates to computer-controlled biological instrumentation, and in particular to controlling information flow to and from biological instruments.

2. Description of the Related Art

Biological laboratories, in particular those focused on genetic and molecular biological work, employ a wide variety of instrumentation in order to perform experiments and analysis. A given test, or assay, may require, as an example, the use of an electrophoresis component, a thermalcycler component, a mass spectroscopy, and/or a gene sequencer. To further complicate matters, some assays require the manipulation of hundreds if not thousands of separate physical samples, each of which is desirably processed through a complex battery of tests, the collected data from which must then be analyzed by secondary analytical instrumentation before creating the intended result. In addition, the physical and logistical demands of the laboratory increasingly require the use of robotics as well as human participants in order to locate and deliver samples to the proper instrumentation.

The necessary complexity of the laboratory situation is worsened further by the difficult nature of communication. Each instrument, robot, and hardware or software application has input and output parameters/information which must be properly configured in order to be utilized. This may include experiment(al) parameters, commands, or catalog information. Unfortunately, because not all biological instruments were designed to communicate with each other, human intervention is frequently required to coordinate the activities of each instrument. Normally, a centralized information flow control system would be desirable in order to reduce human requirements and errors. However, because a particular laboratory environment may contain many different instruments, produced by different manufacturers and with different requirements, it is difficult to integrate instruments as they exist into a unified system. Furthermore, as new instruments are integrated into the laboratory environment with existing systems, additional difficulties may be encountered due to configuration limitations arising from a previous laboratory setup.

SUMMARY

The aforementioned needs are satisfied by the assembly of the present invention which, in one aspect, is comprised of a control and communications system for a biological laboratory having at least one sample analyzer and biological data processor. The system comprises a client component having a user interface that allows a user to gain access and control or monitor the operation of biological instruments in the biological laboratory. It also involves a plurality of instrument components associated with each of the plurality of instruments.

The plurality of instrument components includes a sample analyzer that receives commands selected from at least one pre-set list of commands from the control system and translates the commands into a format that induces an associated sample analyzer to obtain identification information about the biological sample. An instrument component for biological data processor receives commands selected from at least one pre-set list of commands from the control system and translates the commands into a format that induces an associated biological data processor. The data processor analyzes the identification information obtained by the sample analyzer and provides signals indicative of the analysis.

The central management also includes at least one directory that provides information to the client component as to the logical location of the plurality of instrument components. The directory embodiment functions in such a way that the client component can determine how to access the plurality of instrument components by reference to the at least one directory. At least one directory includes information about one pre-set list of commands, at minimum, that the client component can use to send signals to the plurality of instrument components to induce the sample analyzer to obtain the identification information. The sample analyzer will then induce the biological data processor to analyze the identification information.

Another specific embodiment of the central management component is a messaging service that transmits messages to and from the plurality of instrument components and the client component. The messaging service is constructed in a standardized format wherein at least one directory and the client component are configured such that additional instruments can be added to the laboratory. Instruments are added to the laboratory by first associating an instrument component with the instrument itself. The system can then update at least one directory with information about the logical location of the instrument component. This is done so that the client component can become aware of the additional instruments by accessing the at least one directory.

The invention also implements a communications and control system for a biological laboratory having at least one user-interfaced client for controlling and monitoring biological assays and a plurality of instruments, each with at least one associated logical component, for obtaining identification information about biological samples.

The control system is comprised of a plurality of logical components for the instruments that receive commands from the laboratory management system and instruct the plurality of instruments to process at least one biological sample. The plurality of logical components include at least one sample analyzer logical component for at least one sample analyzer that receives commands from the management system. The at least one sample analyzer is instructed by the at least one sample analyzer logical component to obtain identification information about the biological sample.

Another aspect of present invention is a central management component in communication with the laboratory management system, wherein the central management component identifies at least one pre-defined set of instrument instructions for controlling the operation of the plurality of instruments or for communicating with the plurality of instruments. This central management component has at least one data structure that identifies the logical location of the plurality of logical components including the at least one sample analyzer logical component. In one specific embodiment, additional instruments having associated logical components can be added to the management system by updating the data structure as to the logical location of the logical component of the additional instrument. The logical components can be added such that the management component is made aware of the logical location of the logical components associated with the instrument, and the additional instrument can be controlled by a user via the user-interfaced client that is connected to the central management component. This can be accomplished by allowing the user-interfaced client to become aware of the additional instrument by accessing the data structure of the central management component.

The present invention also presents a method of controlling the operation of a biological laboratory. The method involves associating an instrument component with a biological sample analyzer such that the instrument component translates received instructions to the biological sample analyzer. The biological sample analyzer can then be instructed to capture identification information about a biological sample.

Another specific aspect of the method is associating an instrument component with a biological data processor such that the instrument component translates received instructions to the biological data processor. This allows the biological data processor to be instructed to analyze identification information captured by the biological sample analyzer. In addition, the method also maintains a directory of the logical location of each of the instrument components within the laboratory such that a user interface can determine, by accessing the directory, how to access an instrument to implement a process.

The method will also add an additional instrument into the biological laboratory by associating an instrument component to the newly added instrument and updating the directory as to the location of the instrument component. This allows the new instrument to be discovered and accessed by the user interface to implement a process by using the directory. These and other objects of the present invention will become more fully apparent from the following description taken in conjunction with the accompanying drawings.

BRIEF DESCRIPTION OF THE DRAWINGS

A computer-implemented biological data collection and analysis system will now be described with reference to the following drawings:

FIG. 11 illustrates an example list of functions enumerated in a instrument service provider interface.

FIG. 13 illustrates an example set of XML data describing container settings for a biological instrument.

FIG. 14 illustrates an example set of XML data describing manual control parameters for a biological instrument.

DETAILED DESCRIPTION OF CERTAIN EMBODIMENTS

Embodiments of the present invention are directed toward providing an open framework for biological instrumentation and analysis. As will be described below, embodiments of the present invention provide an open, extendable system for performing biological data collection and analysis. Further, embodiments of the system provide for various levels of abstraction of biological instrumentation, along with mechanisms for remotely discovering instrumentation requirements and results formats without requiring direct communication with individual instruments. Thus, wide varieties of instruments, including ones not yet created, can be introduced to the system without requiring lengthy setup time inefficient use of computing and human resources.

Figure 1:
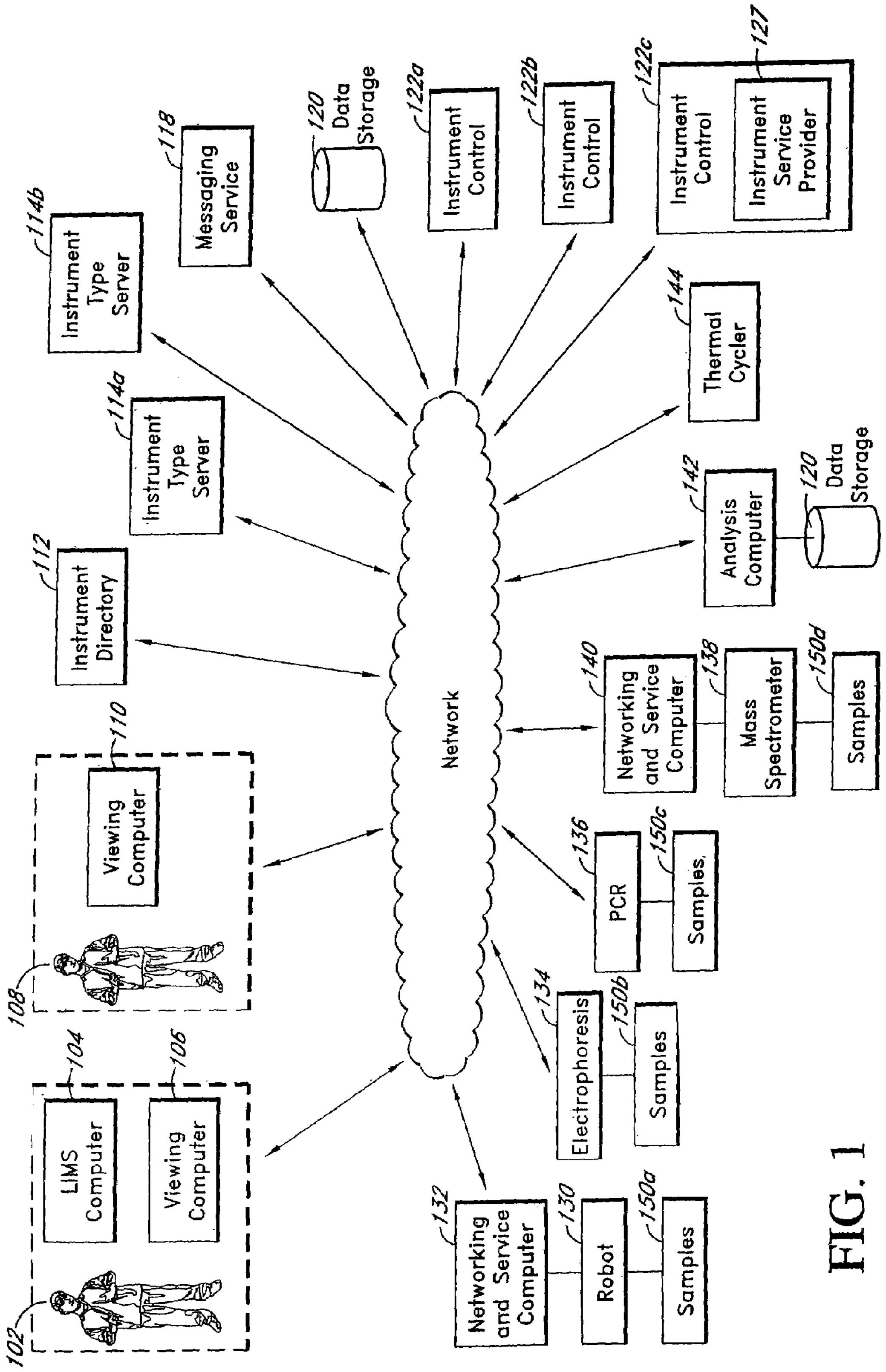
FIG. 1 illustrates an example block diagram for an open system for controlling and monitoring biological data collection and analysis instruments over a network.

Referring to FIG. 1, a block diagram of the open framework system is illustrated. A network 100 provides connection between the various components of the system. The composition of the network 100 can vary and can be, by way of example, the Internet, a wide-area network, a local-area network, or a local Ethernet network. Unless otherwise indicated, the functions described herein are preferably performed by executable code and instructions running on one or more general-purpose computers. However, the present invention can also be implemented using special purpose computers, state machines, and/or hardwired electronic circuits. The term computer can include one or more co-located or geographically distributed computers.

In the illustrated embodiment, a principal investigator 102 inputs a series of data collection and analysis tasks, a "workflow," to a computer 102 running a laboratory instrument management system, or "LIMS." The principal investigator is generally the person with the primary control over the types of experiments performed in a lab and the direct research will take. Besides the LIMS computer, the principal investigator 102 utilizes a viewing computer 106, which provides reports on experiments and data collection. By utilizing the illustrated embodiment and thus being freed from having to control instruments individually, the principal investigator 102 is able to perform some, or all, laboratory experiments using only the LIMS computer 104 and the viewing computer 106.

A laboratory manager 108 is also illustrated, along with a second viewing computer 110. The laboratory manager has the principal task of monitoring the progress of data collection and making sure that the lab's instrumentation is in proper working order. While the principal investigator 102 utilizes the viewing computer primarily for the monitoring of data acquisition and analysis, the laboratory manager's viewing computer provides status reports on the various instruments connected to the system. By utilizing the system in this manner, the laboratory manager can monitor the state of an entire lab from a central location, making it less likely that instrument errors or maintenance needs will be missed.

The system also comprises software components which provide for instrument abstraction and instrument lookup. The first illustrated software component is the instrument directory 112, which maintains basic registration information about instruments connected to the system. The information maintained by the registry typically includes types of interfaces each instrument supports, instrument-specific information such as serial number and physical location, and identifiers and network locations of each instrument's service providers, as will be explained. In one embodiment, the instrument directory 112 also keeps track of the availability of instruments, deleting instrument records as instruments become inactive or go offline.

The instrument directory 112 also maintains information which can be used to locate instrument type servers on the network. The instrument type servers have the primary responsibility of maintaining and providing information about types of instruments rather than instruments at the individual level. Instrument type servers are represented in FIG. 1 as instrument type servers 114*a* and 114*b*, although other embodiments may include fewer or greater numbers of instrument type servers. The instrument type server provides the LIMS computer 104 information about instrument requirements, such as containers or assays that are supported by the instrument, so that the LIMS can prepare appropriate inputs for instruments. Additionally, instrument type servers provide parameters for manual control of instruments. The mechanisms of both the instrument directory and the instrument type server, as well as instrument abstraction and interfaces, will be described in greater detail below.

A messaging service 118 is also illustrated in FIG. 1. As will be described in greater detail below, the messaging service provides the system a mechanism whereby control messages and results can be sent between the LIMS software, the instrument directory, any instrument type servers, and the various instruments without requiring direct communication between components. The messaging service provides a common interface whereby the components can asynchronously send messages between each other without sacrificing resources. Optionally, a data storage device 120 is included in the system for remote storage of results after data collection. Optionally, data is stored locally with the instruments. Another non-instrument component of the system are the instrument control computers 122. These computers contain service provider software 123 which provides control over the instruments as well as provide status updates to the system. As will be described below, service providers implement one or more pre-determined software interfaces which other system components can use to communicate with an instrument in a way that will be understood by each component. While each instrument typically has at least one service provider associated with it, in some embodiments an instrument is controlled or monitored by more than one service provider. The multiple service providers are allowed to run on separate machines. The control of instruments is described in greater detail below. Typically, most instrument communication is done via the instrument control computer, which relays this information to the instrument itself.

The system optionally comprises at least one instrument. Examples of these instruments are illustrated in FIG. 1 in blocks 130, 134, 136, 140, 142, and 144. Some instruments, such as robotics apparatus 130, electrophoresis system 134, thermalcycler system 136, and a mass spectroscopy system 138, have associated biological samples 150 from which they gather data. Other instruments, such as the thermalcycler 144 or the robotic apparatus 130, optionally do not collect data; in the case of the thermal cycler 144, its purpose is to prepare biological samples for further testing by amplifying the material present within the sample. Additionally, the system can optionally provide for instruments such as the analysis computer 142, which perform analysis without requiring contact with physical samples. Instead, the analysis computer mathematically 142 analyses already-collected data 160 to produce its results. In addition, pictured in blocks 132 and 140 are optional networking and service computers. These computers provide for the use of instruments that do not have their own network adapters or communications abilities, by creating a middleware interface between the instrument and the network. Typically, this is done when the instrument was designed to connect to its control computer through a serial interface rather than over a network. This instrument wrapping allows the system to interact with the networking and service computer as if it were the instrument and to not have to take into consideration peculiarities of the instrument's communications system. The instrument wrapping also allows service calls to be made to the instrument from outside the system, allowing a lab manager to check in instrument integrity remotely where otherwise the lab manager would have to perform checks physically at each instrument.

FIG. 1 demonstrates some important and advantageous features of the system. Rather than requiring direct connections between instruments, the system described by FIG. 1 utilizes a network, freeing a laboratory manager from requirements that instruments which communicate with each other must be in close proximity. Similarly, the use of the network allows monitoring laboratory technicians and investigators the freedom to perform assays and check instrument progress remotely. And because each component of the system is connected to the network more or less individually, and not in association with other components, instruments and computers are made easier to swap out and replace or upgrade. The distributed architecture of the system also helps prevent the failure of one component from interfering with the operation of other components.

Figure 2:
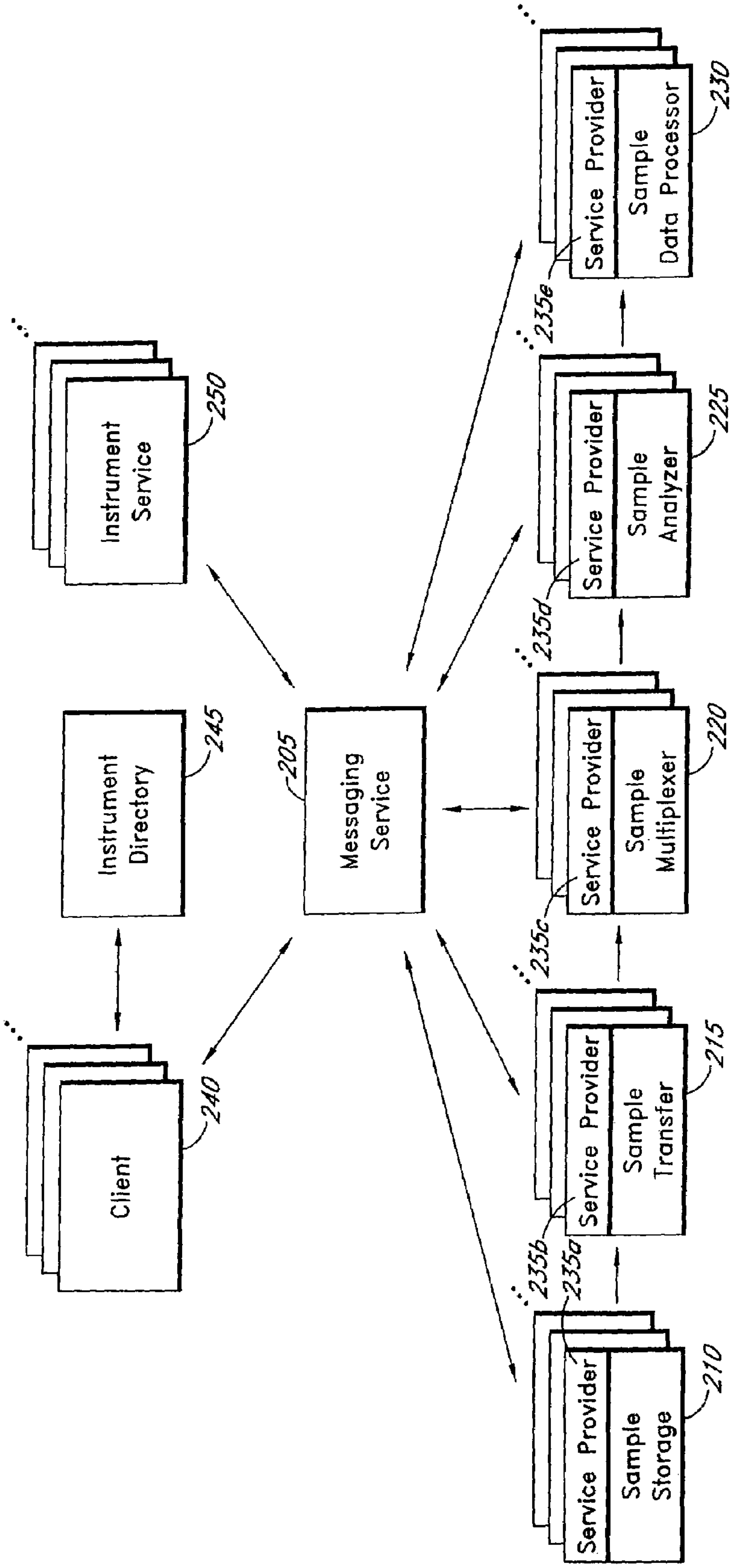
FIG. 2 illustrates an example block diagram for an abstraction of the components of the system of FIG. 1 along with common communications pathways.

Referring now to FIG. 2, a block diagram of abstract system components is illustrated. Various illustrated components are represented as in communication with each other. As represented in FIG. 1, one embodiment of these communications is through a common network using networking protocols such as TCP/IP. In another embodiment, the components may have dedicated connections between each other. The ordering of the exemplary laboratory components 210-230 is meant to represent basic important tools used by most biological laboratory manipulating genetic material in a simple order of use. Each is represented as a possible plurality of tools, and none should be take to represent any particular model or brand of component, but rather a broad class of components. The exact make up of a laboratory will likely differ from the one illustrated in FIG. 2. However, FIG. 2 demonstrates an important inventive aspect of the system in that it abstracts and communicates with each type of instrument in a laboratory, providing control and monitoring throughout the experimentation process.

An exemplary ordering of abstract instruments is illustrated beginning with the sample storage 210. In a typical laboratory the component represented by block 210 would be, in one embodiment, a sample storage room, where biological samples are stored until being located and retrieved for use. The next illustrated component is the sample transfer 215. In one embodiment of a laboratory, this is a mechanized robotic apparatus which locates biological samples through the use of automated indicators, such as a bar code system. Next a sample multiplexer 220 is illustrated. In one embodiment this block represents a thermal-cycler system, which allows biological samples to be amplified in number or quantity before being analyzed. Next illustrated is a sample analyzer 225, which can take the amplified physical sample from the component 220 and analyze it to produce digital data describing the sample. One example of this would be a gene sequencer; another would be a bio-informatics platform. Block 230 illustrates a sample data processor, which processes digital data taken from analysis machines and produces data describing secondary characteristics. And example of this type of component would be a mutation analyzer.

Associated with each of the components 210-230 is an illustrated service provider 235, which provides translation and communication for the instrument, in methods that will be illustrated later. These service providers are in communication, in turn, with the messaging service 205, which provides a general routing and clearing house for communications in the system. In one embodiment, the messaging service 205 is provided by a server implementing the Java Messaging Service® protocol. The use of the messaging service 205 provides easier expandability and quick connection to the system by allowing components to communicate without making direct connections between each other for most communications. Exemplary processes of sending messages through the messaging server are represented below in the discussion with respect to FIG. 4.

The messaging service is also in communication with at least one client component 240. In one embodiment, a client component represents a laboratory management system, such as the LIMS computer 104 illustrated in FIG. 1. The at least one client component 240 also represents viewers, such as viewing computers 104 and 110 in FIG. 1. The at least one client component 240 is also in communication with the instrument directory 245, which stores and serves information about particular instruments; this corresponds to the instrument directory 112 in FIG. 1. Direct communication with the instrument directory 245 is useful in one embodiment because the directory holds network addresses which are needed when sending messages through the messaging service, as will be described below. More contents of the instrument directory will be described in greater detail below in the discussion with respect to FIG. 4.

Also illustrated is at least one instrument type server 250, which corresponds to the instrument type servers 114*a* and 114*b* of FIG. 1 and serve information about types of instruments to clients. These type servers are also in communication primarily through the messaging service 205. Not illustrated are certain limited communications between the instrument directory 245 and the at least one type server 250 and instrument service providers 240 for the purposes of registration. Similarly to the direct communication between clients and the instrument directory mentioned above, these limited communications are allowed so that the instrument directory can remain available independently of the messaging service. This is done so that communication can happen before addresses are known to the directory or messaging service, or while addresses are changing, which may cause messaging service confusion. The various communication processes between these components will be described in greater detail below.

While FIG. 2 represents components of the system in an abstract way, it demonstrates a chief advantage of the open framework in that instrumentation is accessed and communicated with through consistent software pathways, e.g. the messaging service 205 communicating with the service providers 235. And because the system can support most types of instrumentation, as exemplified by components 210-230, the messaging diagram of FIG. 2 is able to support the majority of control and monitoring work in any laboratory. Finally, the use of a messaging service means that components need to maintain very little information about each other or the networks on which they communicate, allowing simpler interoperability and addition of new components.

Figure 3A:
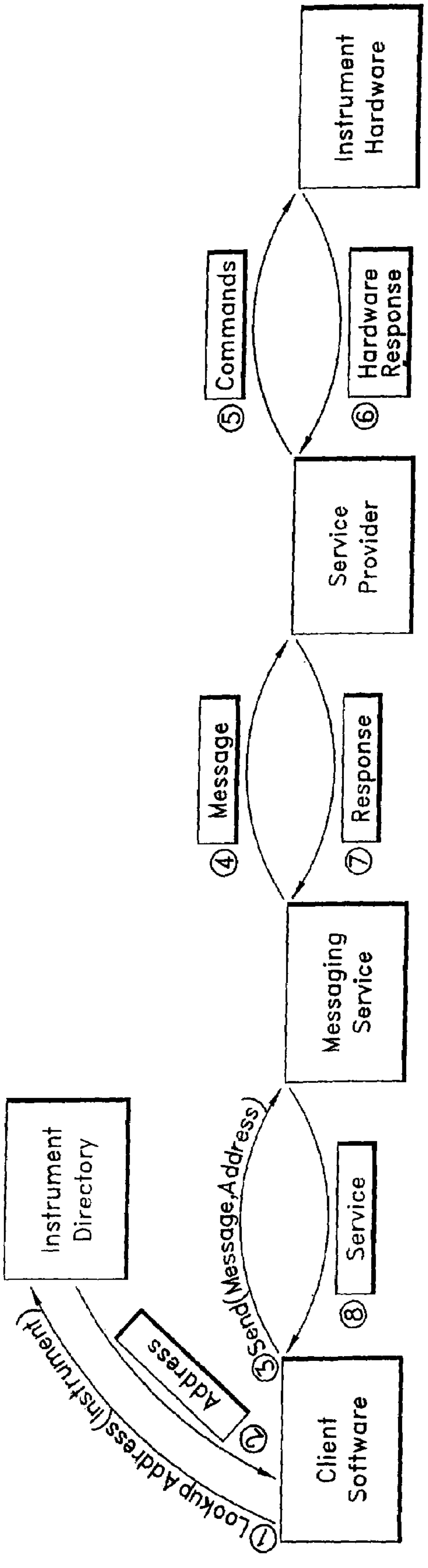
FIGS. 3A and 3B illustrate example block diagrams describing two exemplary messaging processes.
Figure 3B:
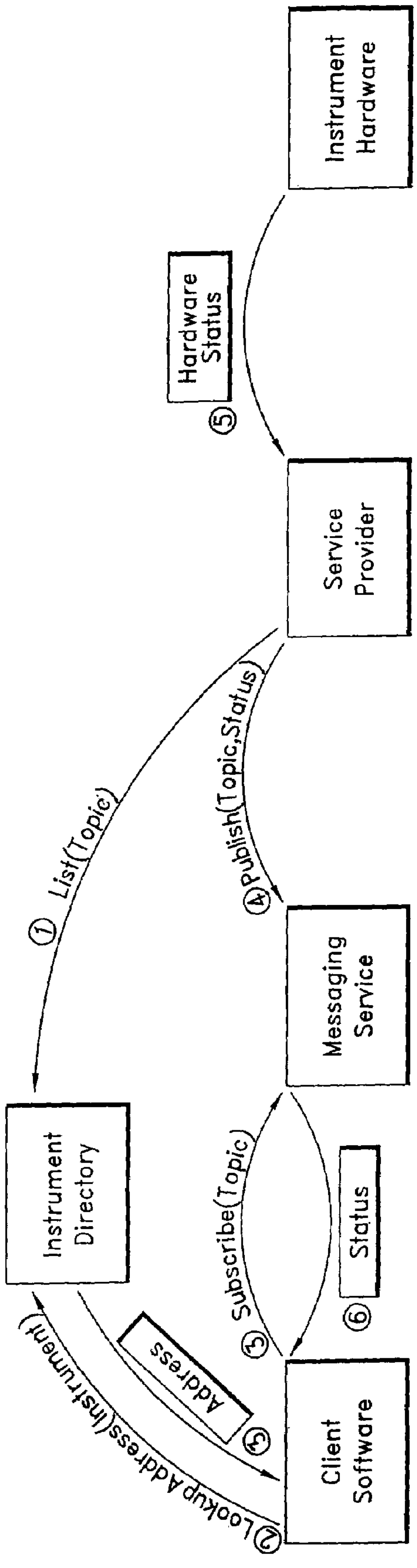

Referring now to FIG. 3, a block diagram is illustrated demonstrating two exemplary messaging processes utilizing the message server. While the message passing in FIG. 3 illustrates one embodiment of system, other embodiments may combine steps or add new ones. The Point-to-Point Messaging process illustrated in FIG. 3*a* is commonly used when one member of the system, in this example a client, wants to send a message to another component, in this example an instrument. One particularly useful method of point-to-point messaging is the request/response method, whereby a request for an action is sent to a message receiver with the expectation that a response will be returned. The response can alternately contain new information, the status of the request task, or an acknowledgement message. In the example given in FIG. 3*a*, a message is sent from a client in order to send a command request to an instrument; this is followed by a response sent back to the client. The use of requests followed by responses is well known. In one embodiment, the client sending the request pauses any computation it is performing while waiting for the response; in another, the client continues with its processes while waiting for a response. In other embodiments, the message is not a command request, but rather information sent to the receiving component. In yet another embodiment, a response is not sent to the originating component.

The illustrated process begins with step 1, where the client software makes a request from the instrument directory to lookup the address of the instrument to which the client wants to send a command request. Continuing to step 2, the instrument directory returns an address to the client. In accordance with the abstraction principles at work in the system, the address given by the directory is that of the instrument's service provider, which is configured to accept messages from the messaging service, rather than the particular hardware of the instrument, which may have no knowledge of the larger system. In one embodiment this address is an IP network address. In other embodiments, the address is a system-defined identifier of the instrument, such as a set of one or more descriptive strings, that is later resolved into a network address by the messaging service, as will be understood. Having received the address, the client software then, in step 3, packages the message and address and sends these to the messaging service for forwarding. At this point, the client no longer has to concern itself with delivery of the message and can either wait for a response, or continue any other processing that it requires.

In step 4, the message is packaged and send to the instrument software. In step 5, the instrument software translates the received message into commands that will be understood by the instrument hardware and delivers these to the hardware itself. After processing the commands, the hardware may then give a response in step 6. In one embodiment, this is a data object representing the result of a data processing request sent in the client message. In another, this response is a result code announcing the success or failure of the received commands. In yet another, the response is a standard status report. Because the hardware may not know about the larger system,.this response will usually be in a format defined by the hardware, and thus not necessarily recognizable by the client software. Thus, having received the response, the instrument software then, in step 7, does any translation necessary for understanding of the response and sends the response to the messaging service for return to the client. In step 8, the response is forwarded by the messaging service to the client, which, if it was holding computation while waiting for the response, resumes computation.

Referring now to the Publish/Subscribe Messaging diagram of 3*b*, a process is illustrated whereby a subscriber component, in this example a client, wishes to receive messages as they are made available by a publisher component, in this example an instrument. The publish/subscribe model is commonly used for status or event messages; in the illustrated example a subscription for status messages is used. This method allows the creator of the messages, the publisher, to inform more than one subscriber without having to send multiple messages or know the identity of any one subscriber. One example is a client wishing to know when a lengthy analysis process has been completed by an instrument. In this circumstance, the publish/subscribe method allows the instrument to signal that it has completed to any interested component without having to send a message to each component and while allowing new components to make themselves available for the completion message whenever it comes.

The process starts at step 1 where the instrument software lists topics to which it will be publishing messages in the instrument directory. In the illustrated example, this topic list includes a status topic. Typically, this is done during the instrument registration process, which will be described in greater detail below. As mentioned above, in the discussion with respect to FIG. 2, there are occasional times when instrument software must communicate directly with the instrument directory; in one embodiment the registration process is one of those times. Next, at step 2 the client software requests a list of topics for the instrument from the instrument directory, and receives a list of those topics at step 3. In one embodiment, the topic list contains a general status topic and a general event topic; in another more detailed topics are listed. Next, in a step 4 the client, after deciding which topics it would like to subscribe to, sends a subscribe request to the messaging service. At this point, the client has completed a subscription and can now wait to receive messages from the messaging service.

At some later point, in step 5 the instrument hardware delivers a hardware status report to the service provider. The service provider does any necessary translation or addition of software status indicators and, having previously registered a status topic, then in step 6 publishes the status report to the messaging service under the previously-registered topic name. The messaging service, having previously received the subscription request from the client, then sends the status report to the client software at step 7, completing the process.

FIG. 3 illustrates some advantage of the system over other systems. As mentioned before, the use of a messaging service allows components to communicate without requiring each component to maintain information about the components with which it sends messages. Additionally, the two messaging techniques illustrated provide enough flexibility to allow direct component-to-component information sharing when necessary, while allowing for the more flexible publish/subscribe technique when direct communication is not necessary.

Figure 4:
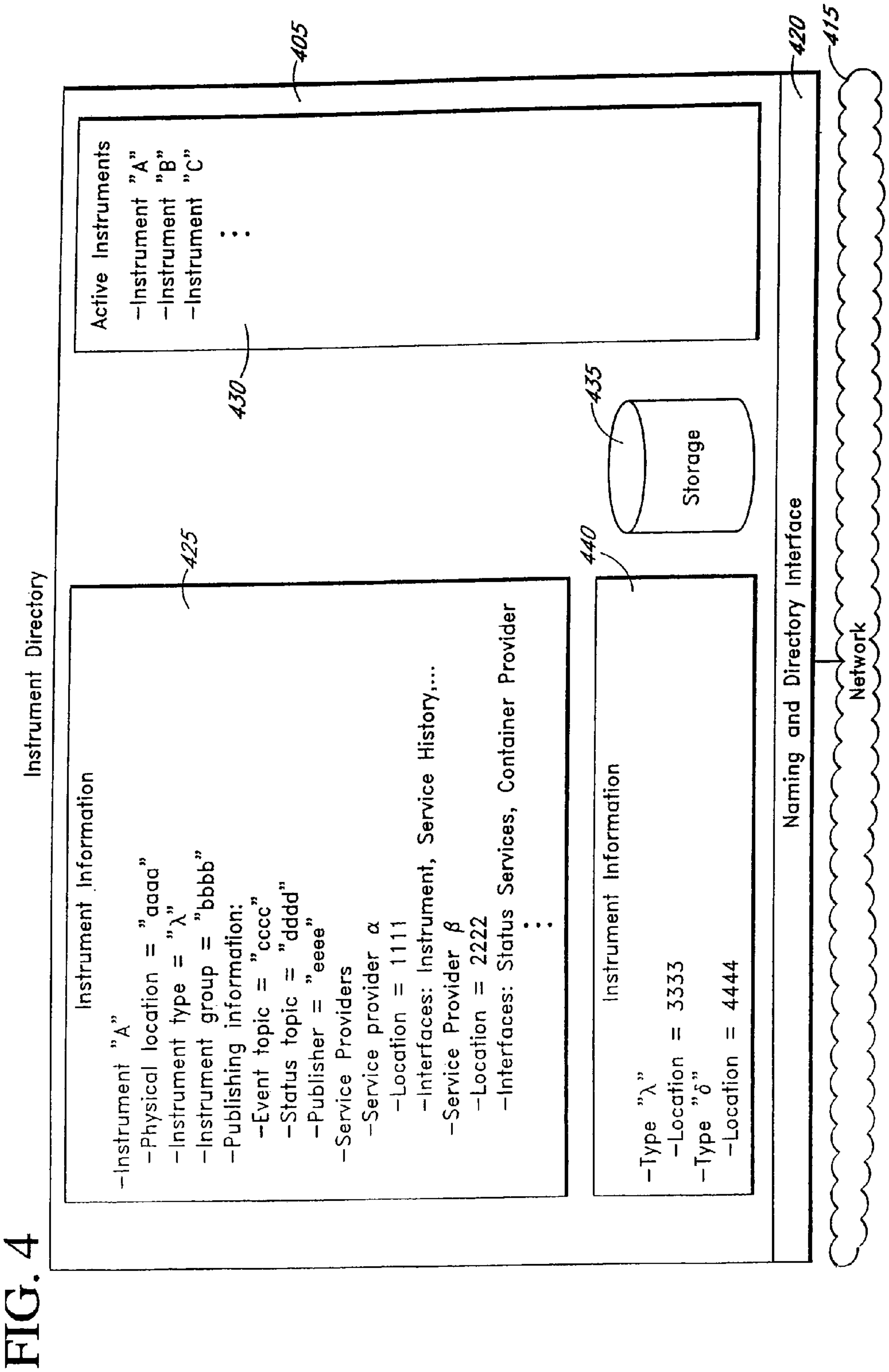
FIG. 4 illustrates an example block diagram describing components of the instrument directory of FIG. 1.

Referring now to FIG. 4, a block diagram is illustrated describing an exemplary instrument directory 405. As mentioned above, the primary purpose of the instrument directory is to contain and serve information about instruments connected to the system to facilitate communication between system components. In the illustrated embodiment, the instrument directory is attached to a network 415, which can be of various networking types, as described above. The networking of the directory is particularly useful because it is in frequent communication with a number of system components in order that those components may communicate with each other. The illustrated embodiment relies upon a naming and directory interface for much of its communication. The use of a naming and directory interface allows system components to use system-specific names which can be translated by the interface into various types of network addressing schemes. Thus, as an example, system components can refer to each other through the use a standardized set of name strings, which the naming and directory interface can then translate into domain name server (DNS) or lightweight directory access protocol (LDAP) names without requiring understanding of these addresses on the part of the system components. In one embodiment the Java Naming and Directory Interface® (JNDI) is used to provide this function. Associated with the naming and directory interface 420 is a data storage 435 which provides a resource for storing various name/address bindings, as well as other information.

One important feature of the instrument directory is the instrument information registry 425, which features detailed information about individual instruments so that system clients may discover which instruments are connected to the system. Illustrated is information for an example instrument "A." In the illustrated embodiment, the instrument information registry maintains a physical location descriptor, here "aaaa." In a typical laboratory, this is done so that a system client can discover whether or not a particular instrument is physically located near a given set of samples and thus is able to process those samples. The inclusion of a physical location indicator increases the utility of the system by allowing it to monitor and control instruments located laboratories that are physically separated with less confusion. The information registry 425 also contains type information, here "λ" and group information, here "bbbb." In one embodiment, this information is used to identify the instrument as one of a general class of instruments and then to unique identify its type. One example would be an instrument of group "electrophoresis" with type "Applied Biosystems 3730." Through the use of these descriptors, a client querying the system for instruments can gain information about every instrument of a particular type or group, filtering out only those instruments which are useful for a particular analysis. The type information is also useful for identifying which instrument type server is associated with the particular instrument, as will be described.

Next, the instrument information lists publishing information. As was described in the discussion with regard to FIG. 3*b*, topic descriptors "cccc" and "dddd" are listed for a particular instrument; in one embodiment these are for events and status information. Also listed in the illustrated embodiment is a publisher name "eeee." The publisher name is included because, as discussed above with respect to FIG. 1, some instruments may utilize more than service provider, and thus it is useful to keep track of which service provider will be publishing for a given instrument.

The final set of information is a list of registered service providers for the instrument. While an instrument can have only one service provider software, the system contemplates that multiple service providers may be used by an instrument, and that they may be executed on different computers at different network locations. Thus, as illustrated, the service provider α lists its network location as 1111. In one embodiment, this is a direct network location, such as an IP address. In another, the service provider location is a system-specific identifier which may be resolved into a network address using the naming and directory interface 420 or the messaging service.

In addition to providing a network address, the service provider information also lists available interfaces for use through that service provider. In one embodiment, these interfaces are pre-determined sets of functions which can be utilized by clients to control or monitor instruments. Because the interfaces are pre-determined and understood by clients of the system, they provide a method by which clients can send communicate with instruments while trusting that their communications will be understood. A few interface types of general interfaces are listed as examples, and not by way of limitation. One interface, the Framework Instrument Interface, is expected by the system to be implemented by at least one service provider for every instrument. This interface provides a common set of instrument control commands to perform activities such as: starting an analysis run, pausing a run, performing diagnostics, getting the instrument status, stopping a run, and shutting down. In one embodiment, the methods in the instrument interface are associated with a pre-determined instrument state model to which it is assumed every instrument service provider will comply. Other optional interfaces which can be implemented are illustrated, such as interfaces to allow access to service history details or instrument status, or to give an instrument information about containers the instrument will encounter in assays. The use of pre-determined interfaces, and their listing on the instrument information registry, simplifies the process of implementing a service on an instrument, as an instrument software developer can know in advance what types of interaction a client will expect from each type of interface. Additionally, should a software developer decide to introduce a previously-unknown type of service at an instrument, new functions or interfaces can be added without the client software needing to understand implementations details.

Besides maintaining information about instrument and instrument service provider details, the instrument directory also provides a list 430 of active instruments. In one embodiment, this list exists so that instrument information can remain in the registry regardless of whether the instrument is available to perform analyses or be monitored. Thus, if an instrument is taken offline for some reason, the instrument can simply send a message to the instrument directory 405 requesting that it be taken off the active list. This will prevent clients from attempting to access the instrument until such a time as it is available again. One examples of a circumstances when this would be useful is the temporary disconnection of an instrument from the network for maintenance or software upgrade.

The instrument directory 405 also contains an instrument type server information registry 440, which contains a list of locations where instrument type servers can be found for each type of instrument. The type servers exist in order to serve clients information about controls available for each particular type of instrument, as well as any containers or assays that an instrument supports. In one embodiment, the types listed in the type server registry 440 correspond to types listed for each instrument in the instrument information registry 425, allowing a client to find an instrument type server for any instrument registered. Much like the service providers listed in the instrument information registry 425, the instrument type servers listed in the type registry 440 implement pre-defined interfaces. In one embodiment instrument type servers are implemented using the same interface objects as are used in service providers. While in one embodiment, separate type servers are used for each instrument type, in others instrument type servers are configured to deliver information about more than one instrument type. In yet another embodiment, a single instrument type server is implemented, the type server having information about every instrument type.

However, because these service providers exist specifically for the purpose of delivering type information, they typically have two pre-determined interfaces. One interface allows for the discovery by clients of supported containers and assays for a particular instrument type. In one embodiment this is done by returning XML data conforming to a pre-defined container and assay schema, upon request. The XML data in this embodiment describes types of containers and assays supported by the instrument type. An example of this XML data will be described in greater detail below. Another interface allows for the discovery by clients of particular manual controls that the instrument type supports. Again, in one embodiment this interface, upon request, returns XML data conforming to a pre-determined schema, the data giving parameters that may be controlled by a client. An example of this XML data will also be described below. The use of type servers to provide type-specific information has a number of advantages over existing systems. First, the use of dedicated type servers reduces traffic to instrument service providers and save computation by the service providers. Secondly, the use of type servers allows clients to learn of updates to a particular type of instruments in one communication, rather than having to query each individual instrument. Finally, because container, assay, and manual control information are typically provided by a type server, a client can discover most of the information it needs to prepare experiments and controls for multiple instruments with very few communications.

Figure 5:
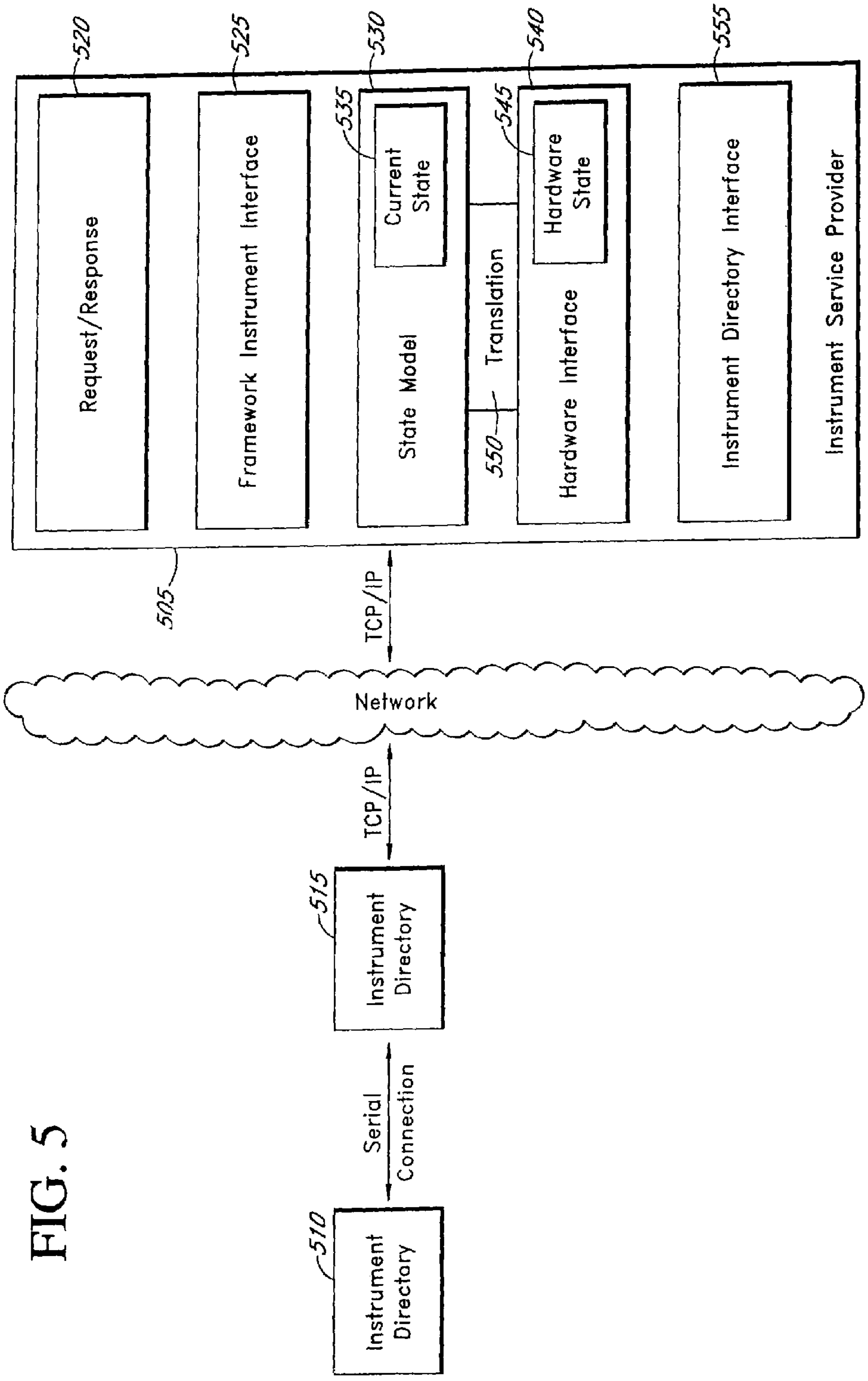
FIG. 5 illustrates an example block diagram describing components of an instrument software interface.

Referring now to FIG. 5, a block diagram of instrument hardware and software is described. An instrument service provider 505 is illustrated, comprising various components that are used in order to provide communication and control with the instrument hardware 510. In addition, networking and service middleware 515 is illustrated. This middleware conforms to the software running on the networking and service computers 132 and 140 as illustrated in FIG. 1, and is used typically to provide networked communications where the instrument hardware was designed with only a serial connection interface. In the example, TCP/IP is used to communicate between the service provider 505 and the middleware 515, however as discussed above, other networking protocols can be used.

The instrument service provider 505 itself comprises multiple software modules. While the software modules are illustrated as separate and distinct, their functions may be combined into fewer modules or broken down into more modules while incorporating various aspects. In addition, the modules may represent differing degrees of execution independence, including separately-running applications, individual process threads, or dynamically-linked libraries being executed by another application. One illustrated software module is the request/response module 520. This module contains software calls and hooks in order to allow messaging to be sent and received from the messaging service. In one embodiment, this software module also controls publication of event and status messages. The framework instrument interface 525 corresponds to the interface discussed above with respect to FIG. 4 which describes functions providing high-level control of the instrument. The service provider 505 also contains a state model 530, which describes at an abstract level a plurality of execution states which any instrument in the framework is expected to conform to. In accordance with this state model, the service provider maintains a record of the current state of the instrument 535. In one embodiment, the functions enumerated in the Framework Instrument Interface correspond with states and transitions in the state model 530. The state model is described in greater detail in co-pending U.S. patent application Ser. No. 10/454,759, filed Jun. 4, 2003 and titled "SYSTEM AND METHOD FOR PROVIDING A STANDARDIZED STATE INTERFACE FOR INSTRUMENTATION" which is herein incorporated by reference in its entirety.

Because the state model 530 is not intended to conform to particular commands of the instrument hardware, the service provider maintains a software module 540 which acts as an interface to the instrument hardware 510. In one embodiment, this module understands the various commands accepted by the instrument hardware 510. In another, the module 540 is able to accept information provided by the instrument hardware, such as status reports. In addition, the service provider maintains the current state of the hardware 545 in order to give contextually-appropriate commands to the instrument. Software module 550 provides translation between the state model and the hardware interface. In one embodiment, the translation module is a mapping between transitions in the state model 530 and pluralities of hardware commands. In another the translation module 550 translates information received from the instrument hardware and modifies it for use with the messaging service. The final illustrated module is the instrument directory interface 555, which provides communication with the instrument directory. A separate interface is provided for directory communication because, as mentioned above, certain direct communications are needed with the instrument directory rather than through the messaging service.

The service provider illustrated in FIG. 5 demonstrates the advantages of the instrument wrapping and abstraction of the system. The numerous software modules of the service provider facilitate communication between clients and instrument hardware through the use of commonly-understood interfaces and messages. By allowing this communication to occur without requiring knowledge of the implementation of any particular instrument involved, the system once again invites simplified introduction and modification of instrumentation.

Figure 6:
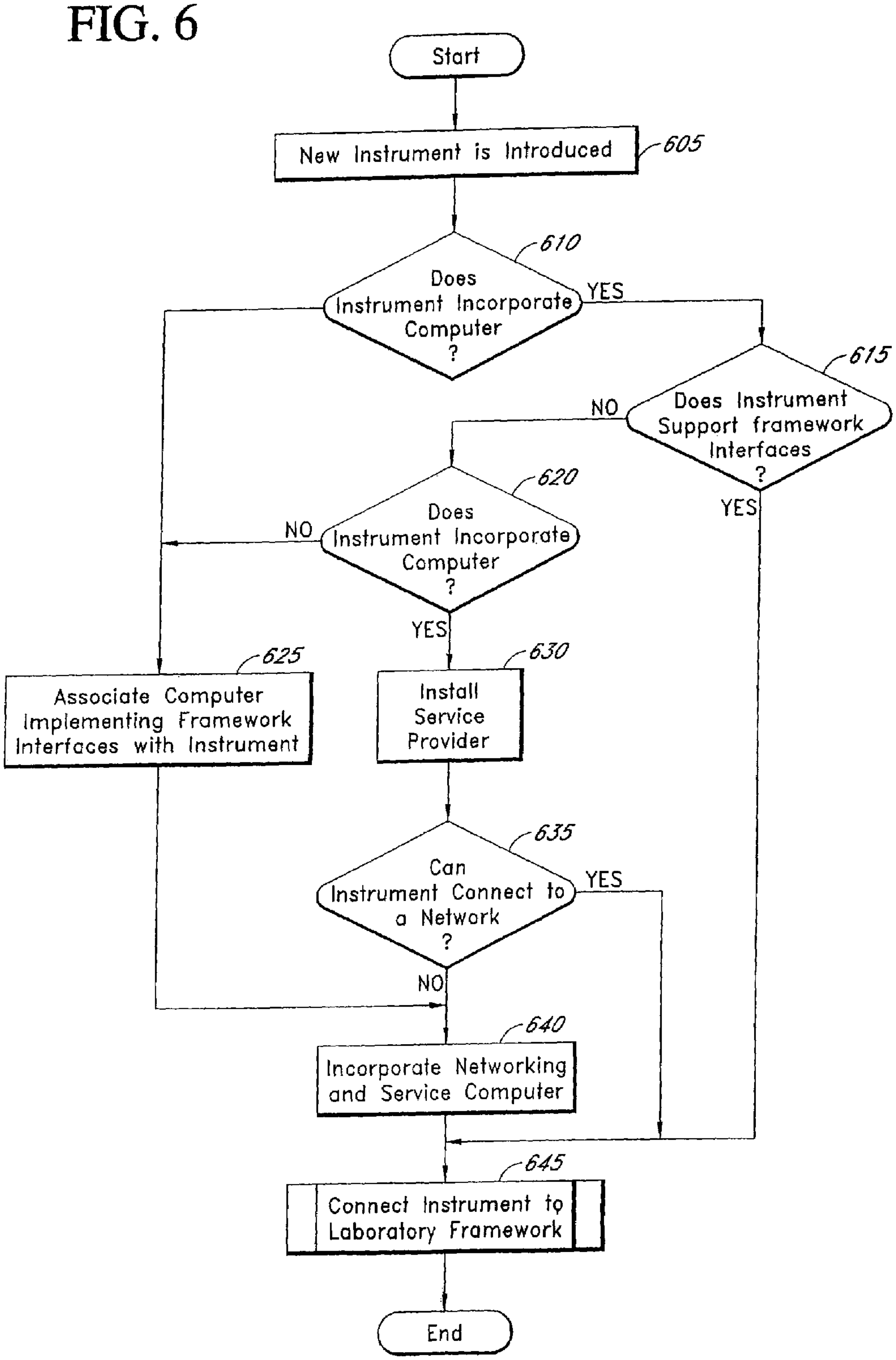
FIG. 6 illustrates an example flowchart of a process that occurs when a new biological instrument is introduced into the system.

FIG. 6 illustrates an example embodiment of a process of introducing a new biological instrument into the system. The process illustrates one advantage of the system in that any instrument can be integrated with the system regardless of whether it has been designed with the open framework in mind or not. Depending on circumstances, the process of FIG. 6 may be performed by an investigator in a lab, a lab manager or technician, a programmer wishing to integrate the instrument into a laboratory using the illustrated system, or even the designer of the instrument itself. Starting at state 605, the new instrument is introduced into the laboratory. The ability of the instrument itself to recognize the open framework system are not important, and it is contemplated that instruments will vary. Some added instruments will be designed specifically with the open framework system in mind. Some instruments will pre-date the system or have control and monitoring systems designed without regard to being included in the illustrated framework. Other instruments will be duplicates of instruments already introduced to the laboratory. The term instrument will be used generally in the following discussions, so as to be inclusive of each of the various types of instruments mentioned above, as well as unmentioned instruments and biological instruments which are currently undeveloped.

Continuing to state 610, it is determined whether the instrument incorporates a computer. This is done in order to determine if the instrument could already support a computer corresponding to the instrument control computers 122 illustrated in FIG. 1. The word "incorporate" should be understood to indicate that the instrument utilizes a computer for control and monitoring. Thus the term incorporate includes instruments with an on-board computer, instruments connected through physical serial connections to a computer, instruments connected via a network to an associated computer, and also instruments utilizing a plurality of computers. If the instrument does not incorporate a computer, the process moves to state 625, where a computer implementing interfaces to the open framework system is associated with the instrument. In one embodiment, this is done by providing a computer running an instrument service provider. After associating a computer with the instrument, the process moves to state 640, where a networking and service computer is added to the instrument, so that it can be attached to a network. In one embodiment, the networking and service computer is separate from the computer executing the service provider; in another, they are integrated. The process then proceeds to state 645, where the instrument is connected into the laboratory framework. The particular details of the process of state 645 are described below in the discussion with respect to FIG. 7.

If, however, the instrument does incorporate a computer, the process continues to state 615, where it is determined whether or not the instrument supports the framework interfaces already. One method by which this could occur is if the instrument integrates a service provider. If the instrument does support the interface, the process proceeds to state 645, where the instrument is connected into the framework. If the instrument does not support the interfaces, the process continues to state 620, where it is determined whether or not the instrument interface can be modified to support the open framework. An example of an instrument that could support the interface would be an instrument which partially comprises a computer and for which a service provider has already been written, either by developers of the instrument who wish to update it or third parties. If the instrument cannot be modified to support the interface, the process continues to state 625, where a computer is incorporated in order to support the interface. If however, the instrument's interface can be modified, the process continues to a state 630, where service providers are installed on the instrument computer, and then to state 645, where the instrument is connected to the laboratory framework. After connecting the instrument to the frame work, the process of FIG. 6 ends. FIG. 6 illustrates the advantageous flexibility of the framework in that instruments with differing degrees of computer integration or framework support can be incorporated into the system. The end result of any path through the process is an instrument that can be understood by the system through easily-understood ways.

Figure 7:
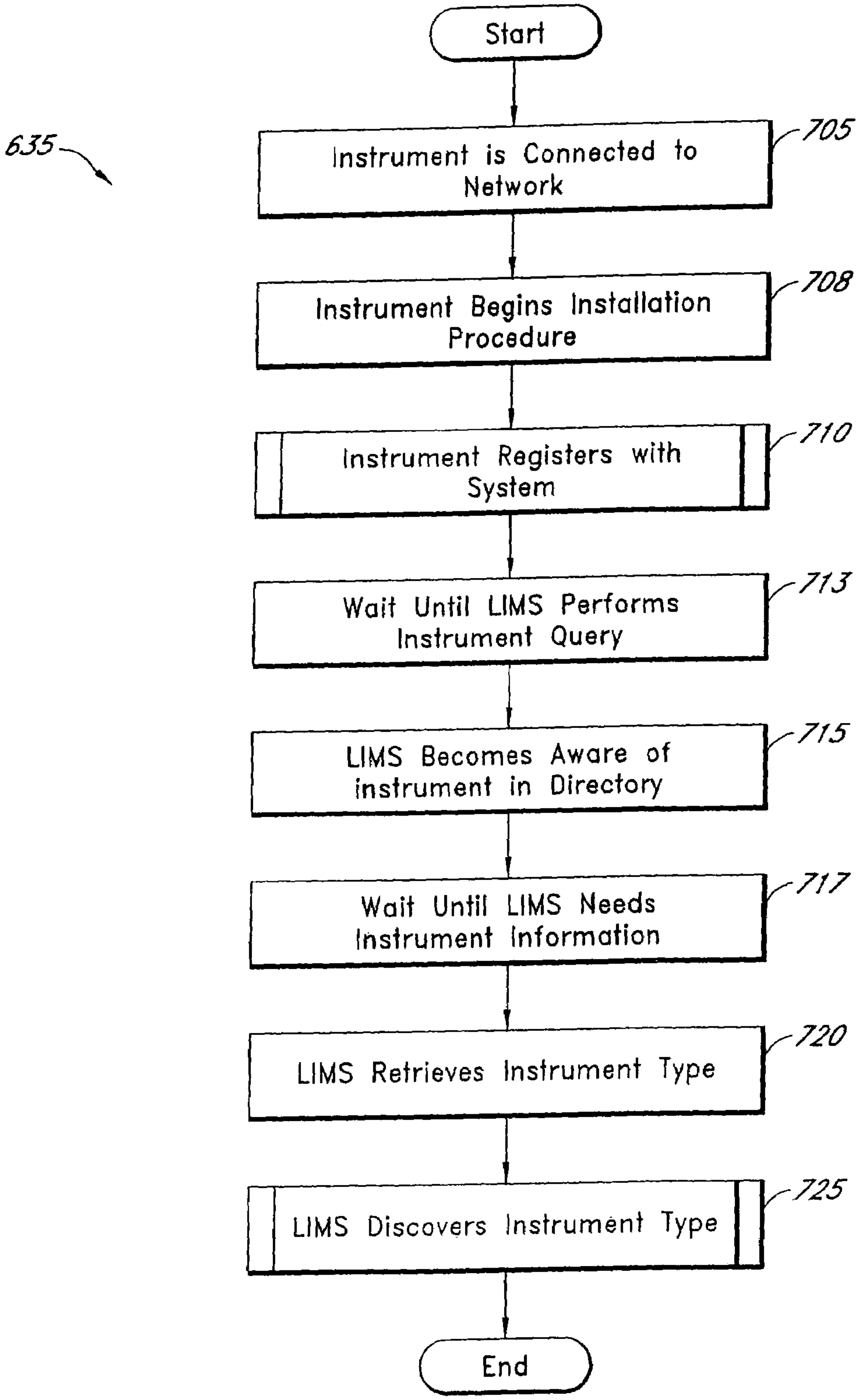
FIG. 7 illustrates an example flowchart of a process that occurs as part of the process of FIG. 5 when an instrument is connected to and registers with the system.

FIG. 7 illustrates an example embodiment of the process of connecting an instrument into the laboratory framework and having that instrument discovered by the LIMS. The process of FIG. 7 corresponds to a process performed in state 635 of FIG. 6. Because some states in the process in FIG. 7 involve determinations by the LIMS in order to continue, delays of differing duration may occur before the continuation of the process at certain points. By including those waiting periods in the process description, FIG. 7 illustrates the ability of the system to provide instruments which are ready to be discovered and used when the LIMS is ready for them, rather than requiring lengthy set up processes. The process starts at a state 705, where the instrument is connected to the network. Depending on the particular characteristics of the instrument, this may involve connecting the instrument itself to a network, or connecting its associated computer 122 with service provider to a network.

Next, the process continues to a state 708, where the instrument begins an installation procedure. In one embodiment, this can be done through a call to the instruments associated computer 122 and service provider 123. In another embodiment, the framework installation procedure occurs when the service provider software itself is installed on a control computer 122. In another embodiment the installation occurs when the service provider software is installed on the instrument itself. In yet another embodiment the installation procedure is performed by a separate installation application. In one embodiment, this installation application also creates the service providers for the instrument. The process continues to state 710, where the instrument registers its type and particular parameters with the open framework system. This process is described in greater detail in the discussion below with respect to FIG. 8. The goal of registration is to provide relevant portions of the open framework with enough information that other instruments and analytical devices can design assays and workflows that make proper use of the instrument without having to query the instrument itself or understand particulars about its implementation. In both these and subsequent states, in the case where the service provider is already up and running, the service provider itself typically does the majority of system communication, sending messages to the actual instrument only when necessary. Thus, in one embodiment, must of the registration that follows is done by the service provider.

After the instrument is registered on the system, the process waits at state 713 for the LIMS to perform an instrument query. Then the process proceeds to state 715 which is where the LIMS becomes aware that the instrument is in the directory. This can happen in a number of ways. The LIMS may query the directory to determine if any new instruments have been added. The LIMS also may query the directory based on other criteria, such as all instruments of a specific type, or all instruments in a specific physical location. In another embodiment, the LIMS may ask to receive updates when new instruments are added to the registry. In that embodiment, as instruments are registered, the instrument directory broadcasts a message informing the LIMS that there is a new instrument available for use.

Once the LIMS knows of the existence of the instrument, it may learn about the instrument to determine if it would be useful for a given workflow or assay. Until this time, the process waits at a state 717 for the LIMS to need information about the instrument. Continuing to state 720, the LIMS retrieves information from the directory relating to the network location of the service provider implementing the interface through which the LIMS wishes to communicate. Next, at state 725, the LIMS discovers the instrument's type, in order to create assays that correspond to the instrument. Further explanation of the type discovery is described below in the discussion with respect to FIG. 9. After discovering the instrument type, the process of FIG. 7 ends.

Figure 8:
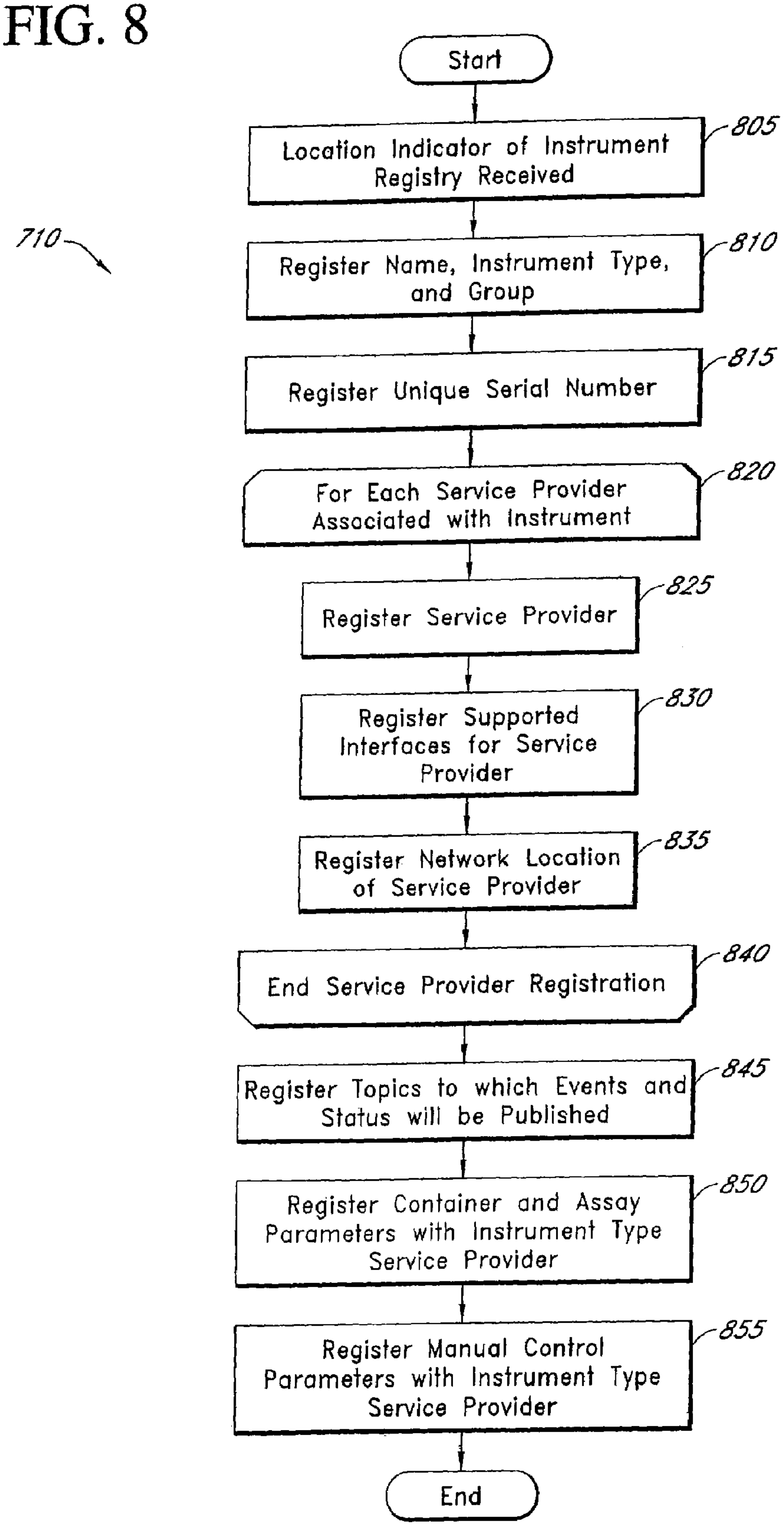
FIG. 8 illustrates an example flowchart of a process that occurs as part of the process of FIG. 7 when an instrument registers with the system.

FIG. 8 illustrates an example embodiment of the registration process, corresponding to the process of state 710 in FIG. 3. Starting at state 805, an indicator of the location of the instrument directory is received by the installation software. In one embodiment, this indicator is the uniform resource locator of the instrument directory. In another embodiment the indicator is a local area network address. In yet another, embodiment, the indicator is an IP address. This indicator may be entered at different times; in one embodiment it is provided at the time the service provider software is installed, in another, it is provided at a later time, when a laboratory manager or other technician determines that the instrument should appear on the network. Next, at state 810, the installation software registers the name of the instrument, the instrument type, and any groups to which it belongs. The registered name may be any identifier, although a unique name is desirable. The instrument type is an indicator, corresponding to a particular instrument type server, that indicates that the instrument supports all services associated with that type server. The group indicator is used to include the instrument in a general class of instruments; one example would be gene sequencers.

Next, at a state 820, the installation software loops through a registration process for each of the instrument's service providers. In state 825, it registers the name of the service provider with the instrument directory. In state 830, it registers indicators of the interfaces that service provider supports. While it is expected that one of the service providers for each instrument will support the Framework Instrument Interface, other interfaces are optional. The installation software then registers the network location of the service provider with the directory so that it can be found for later communication. Then, at state 840, the process repeats for each unregistered service provider.

Once each service provider is registered, the process continues to state 845, where the installation software registers topic names to which events and status messages will be published, as discussed above with respect to FIG. 3. Next, the installation software, at state 850 registers container and assay parameters with the instrument type server for that instrument type. In one embodiment, if no type server exists for that instrument type, one is created and registered with the instrument directory. An example of a format of container and assay parameters is given below. Then, at state 855, manual control parameters are registered with the instrument type server.

Figure 9:
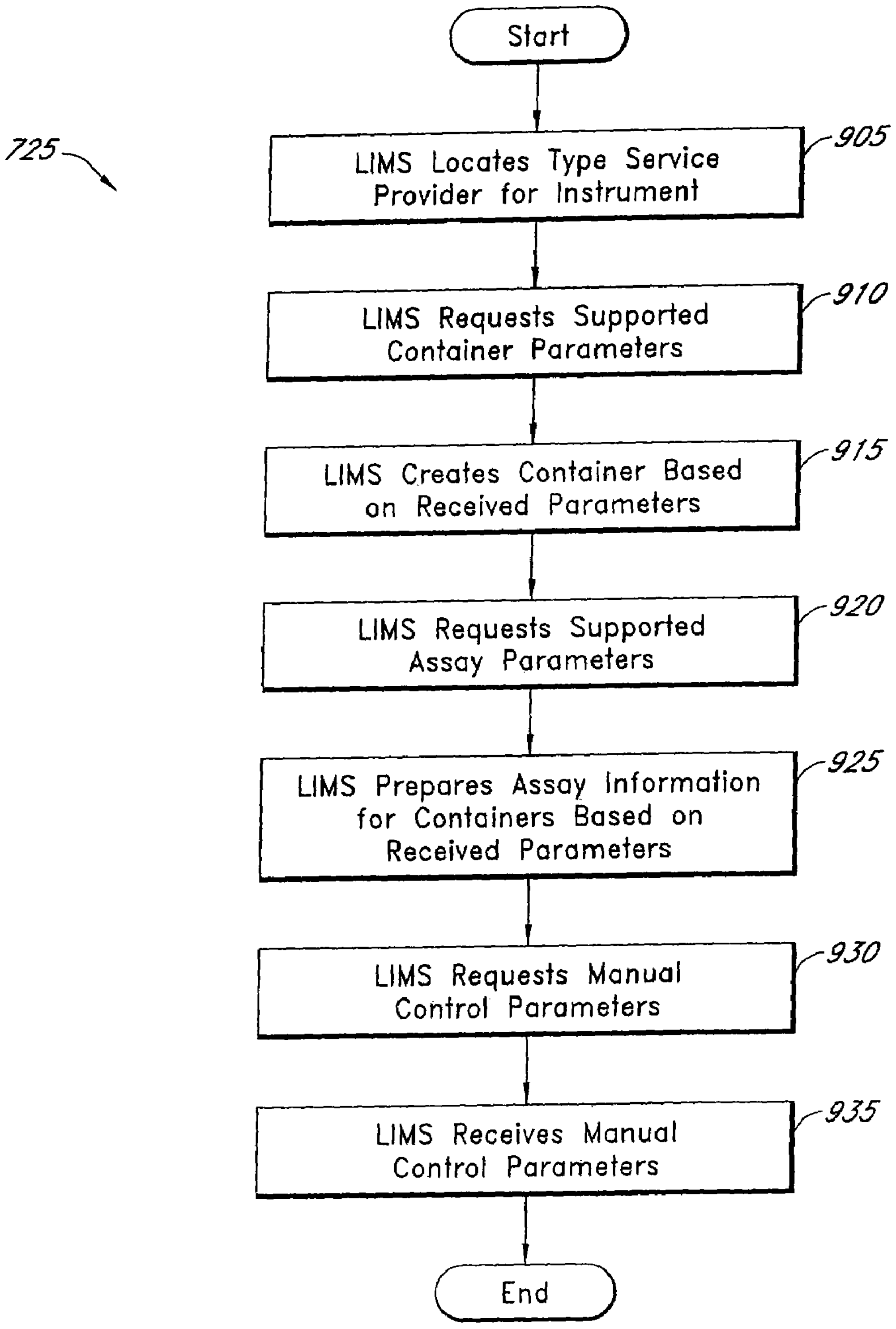
FIG. 9 illustrates an example flowchart of a process that occurs as part of the process of FIG. 7 when a laboratory management system discovers instrument type information.

FIG. 9 illustrates an example embodiment of a process by which the LIMS discovers instrument type parameters. Because not all states in FIG. 9 rely on each other for completion, other embodiments of the instrument parameter discovery can omit steps while incorporating inventive aspects. As illustrated in FIG. 7, the process of FIG. 9 can be performed by the LIMS upon registration. In addition, the process of FIG. 9 can be performed at any time the LIMS needs type-specific information about an instrument. Starting at state 905, the LIMS locates the type server for an instrument. As described above, this can be done by querying the instrument directory to provide the address of an instrument type server associated with a specific type. Then, at state 910, the LIMS sends a message to the type server requesting data describing supported container types. Next, at state 915, the LIMS, having received a response containing XML data describing the container types, creates a container based on the received parameters. An example of a container detailed in XML is given in FIG. 12. The process continues to state 920, where the LIMS sends a request to the type server for supported assay parameters and then to state 925, where the LIMS prepares assay information based on the parameter information received in the type server's response. One example of XML assay data is given in FIG. 13. The LIMS then, at state 930, requests manual control parameters from the instrument type server, and at state 935, receives XML data detailing the manual control parameters. One example of a set of manual control parameters is given in FIG. 14. FIG. 9 illustrates the ease of discovering a new instrument in the illustrated system. By reducing the process of receiving information about a instrument into three requests, the system reduces the amount of time needed for setup of an assay. Further, by utilizing XML data conforming to a specified schema for instrument parameters, the system is able to trust that a client will understand an instrument and be able to easily integrate it into assay workflows.

Figure 10:
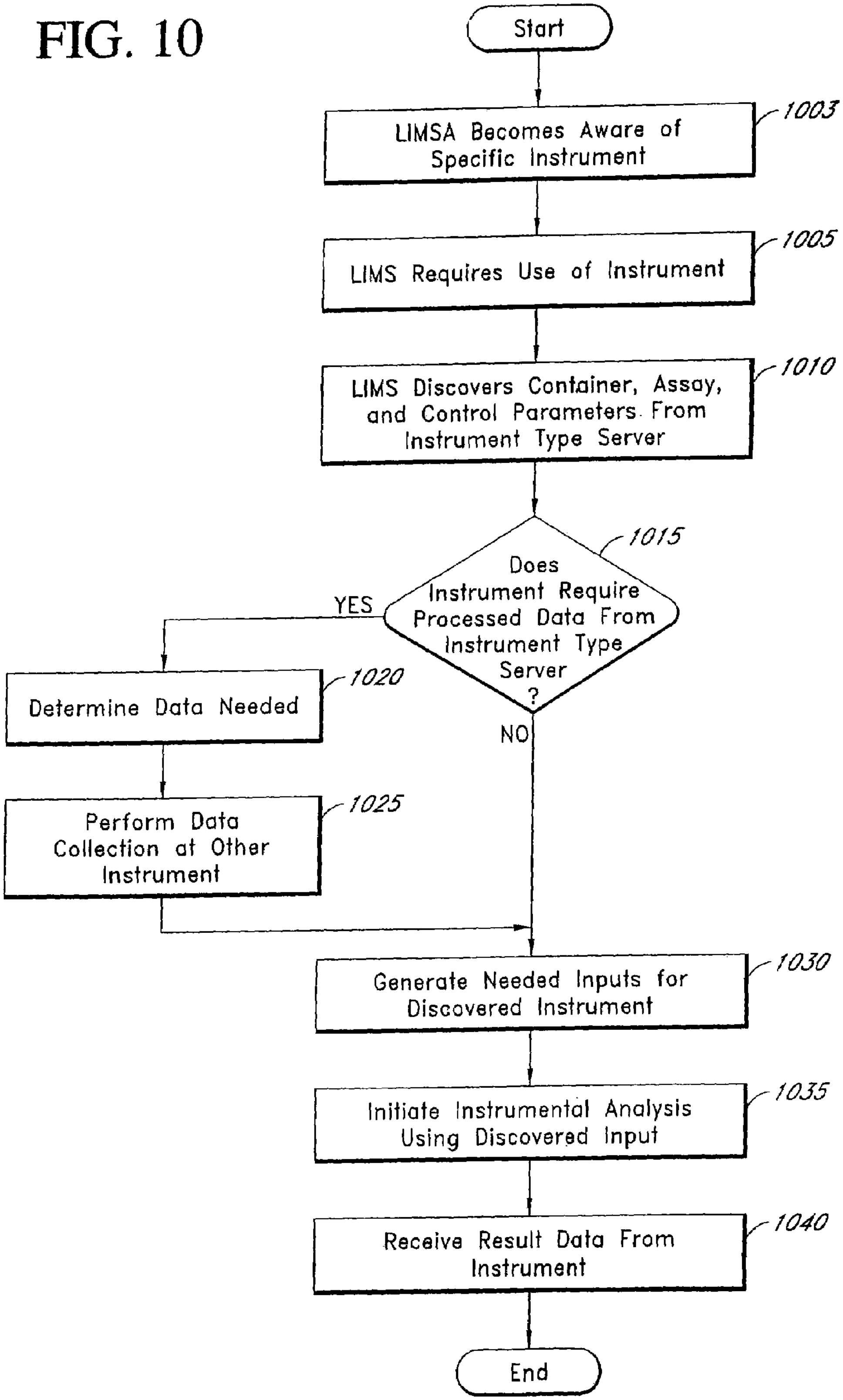
FIG. 10 illustrates an example flowchart of a process that occurs when the system uses a connected and registered instrument to collect data results.

FIG. 10 illustrates a high-level process that occurs as a client, such as the LIMS, utilizes the open framework to perform an assay. The process illustrated in FIG. 10 demonstrates the ability of the open framework to automate and simplify the process of running assays in a biological laboratory. Beginning in state 1003, the LIMS becomes aware of a specific instrument connected to the framework system. As mentioned above with respect to state 715 of FIG. 7, this can happen through querying the instrument directory or by receiving an indication that a new instrument has been added to the laboratory framework system. At a later point, in state 1005, the LIMS determines that it requires the use of this instrument. Then, at state 1010, the LIMS discovers parameters from the instrument's type server, such as container and assay parameters and manual control parameters. One example of this process is described above with respect to FIG. 9.

Next, at state 1015, the LIMS determines if the instrument chosen at state 1005 requires data processed by another instrument. One example of this would be a software application for mutational analysis, which would require gene sequencer information in order to perform an analysis. In another embodiment, state 1015 would determine that the instrument required physical sample that must be processed in a specific way by another instrument, such as being processed by a thermal cycler. In yet another embodiment the LIMS determines at state 1015 that a physical sample is needed to be retrieved by a specific robot. If this is the case, then at a state 1020 the LIMS determines what data is needed. In one embodiment, this is done by inspecting the container data requested at state 1010. Once the data requirements are understood, at state 1025 the LIMS performs data (or sample) collected with the instrument identified at state 1015.

Whether another instrument was required at state 1015 or not, the process goes to state 1030 where the LIMS generates appropriate inputs for the instrument. In one embodiment, this preparation is based on parameters discovered at state 1010. The process then continues to state 1035, where the LIMS, utilizing either the Framework Instrument Interface or parameters discovered at state 1010, initiates analysis by the instrument. In other embodiments state 1035 may conform to commanding non-analytical processes, such as for a thermal cycler or a robot. Finally, at state 1040, the LIMS receives data from the instrument. FIG. 10 illustrates the simplicity of controlling and preparing an assay under the open framework. Because common interfaces are used, the process is relatively similar for any type of instrument, regardless of the analysis or task it performs. Additionally, the process of FIG. 10 illustrates the ease of integrating the output of one instrument with the requirements of another, and in an automated way that can reduce human error.

FIG. 11 illustrates exemplary functions implemented in one embodiment of the Framework Instrument Interface. While some embodiments utilize additional software interfaces for instrument control and monitoring, the Instrument Interface is provided here as an illustration of the types of functions that may be enumerated in an interface. The Framework Instrument Interface is one of the interfaces that a service provider may provide in order to allow for control and monitoring of an instrument at the abstract instrument state model level. As the other interfaces implemented by service providers, clients call functions in the interface through messaging requests to an instrument's service provider. In one embodiment, every instrument is expected to implement the functions enumerated by the interface.

Because the Interface is intimately associated with the state model, some functions illustrated in FIG. 11 correspond to commands to transition between states in the instrument state model. One example of this is function 1155, StopImmediately(), which causes an instrument to immediately cease whatever analysis task it is currently performing and transition to from the Pauseable state into the Abort state. Other functions illustrated in FIG. 11 perform status tasks, such as function 1105, GetInstState(), which returns an instrument's state to the requesting client, or function 1110 GetInstStatus(), which returns a status response message to the requesting client. In one embodiment, function 1120, ManualControlCommand(), has a special role. It is utilized to pass a command code, usually in the form of a string, to the instrument in order to execute a manual control command. Thus, through function 1120, a client can issues commands in a more direct manner to the instrument, without being constrained by the state model. This is necessary for instrument-specific commands, and, as mentioned above, the parameters used to create a manual control command are received by a client by calls to the instrument's associated type server. The use of this particular interface is advantageous in that it provides for a commonly-understood set of commands that work across all instruments. By tying the commands of the Framework Instrument Interface into the universal state model, a broad-based method of control is created that any client can trust in. This makes instrument addition to the system easier for clients, as they can trust that, at a minimum, certain functions will be supported by any new instrument.

Figure 12:
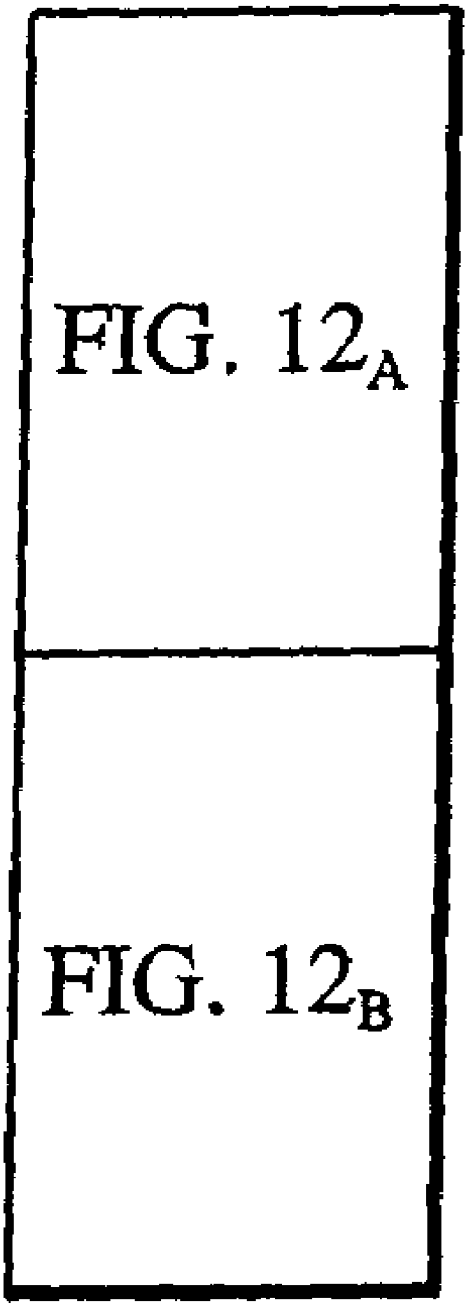
FIGS. 12A-B illustrate an example set of XML data describing container parameters for a biological instrument.

FIG. 12 illustrates an exemplary piece of XML data that describes parameters for a particular container and assay. The piece of data illustrated in FIG. 12 is cut from a larger piece of data for ease of explanation; thus the example data is not necessarily representative as a complete container and assay data sample and is not necessarily in proper XML format. Additionally, only a few types of parameters are represented in the Figure as examples; this does not limit the number or type that can be used in an implementation of the system. While the use XML data to describe container, assay, and manual control parameters is advantageous because XML lends itself to extendibility, other data types may be used while incorporating inventive aspects. Typically, the parameter data illustrated in FIG. 12 would be gained by a client by querying an instrument type server. This process of querying and receiving data would conform to steps 910-925 of FIG. 9. Upon receipt of this data, a client would be able to create containers and assays for use in the queried type of instrument by interpreting the parameters listed in the data. In addition, the data also contains information which can be used to create a graphical user interface for the particular type of instrument. One the client had determined available parameters for the container and assays for that instrument, the client would then be able to create a set of XML data describing the particular containers and assays to be used.

Section 1210 of the data demonstrates descriptor parameters used to identify a container. The descriptor parameters can also be used in a graphical user interface used to set container information. Thus columns, such as "Container Name," "Container Barcode ID," and "Comment" are suggested for any user interface used to create containers. This is done in order that a lab technician creating a set of containers for testing will know which pieces of identifying information are necessary for proper tracking of the containers. Next, the data defines a number of entries that describe necessary container information parameters. Each parameter comprises a section similar to sections 1215, where descriptors for that parameter are listed. In section 1215, the container information is revealed to be the type of plate that is to be used in the instrument. Then, in section 1220, specific different values are given for this parameter; in this circumstance the client is given a choice between identifying a 96 well plate type of container or a 384 well plate type of container. If a graphical user interface is created from this XML data, this section could be used to create a set of selection buttons or a drop down menu from which a lab technician could describe the type of plate that comprises the container.

Section 1225 demonstrates a different type of parameter. In this section, rather than define specific parameter values, the path of a Java class is given. Thus, in the illustrated embodiment, a client could create a software object instance of the Java class listed, and then use this class's methods to populate assay data for that container. Other embodiments may use different programming languages, as will be understood. This is advantageous over listing specific values as it allows complex data collection to be handled by software, simplifying the XML data, and allowing for the client to use the enumerated class to perform necessary calculations to create parameter data. In one embodiment, the class provides a user interface for entering data. In one embodiment, the class provides a method which creates XML data that can be sent to the instrument along with other container and assay parameters at the time an assay is to be performed. In yet another embodiment, a serialized version of the class itself is sent to an instrument's service provider, which is then utilized by the service provider to set instrument parameters.

Section 1230 is similar to section 1220, in that it also describes a list of parameters, this time describing a method of plate sealing for a container, and giving parameters "septa" and "heat seal" as choices. As above, these choices can be represented to a client in a user interface. Moving ahead to section 1235, a third type of parameter is shown. Here, the scheduling preference parameter is allowed to be any integer between a minimum and maximum value; in this case the range is 123-3210. Thus a client can see that a value must be set for this parameter within this range, and provide a user with the prompting to do so. In a graphical user interface, this might be done through the use of an input box or slider tool. FIG. 12 illustrates just a few of the types of parameters that can be included in XML data for a instrument type. By representing parameters in this manner, rather than through less-expandable encoding schemes, the system allows for new types of parameter data to be easily added to the XML descriptions. In addition, by supporting dynamically-created software objects in parameter data, the system prevents the types of data being shared from being limited by any particular form of data.

FIG. 13 illustrates an example of XML data describing a particular container. In one embodiment, this is created by a client after receipt of parameter data, such as in FIG. 12, in order to instruct an instrument of the particulars of a container being used for an assay. The data can then be sent to an instrument or held by a client to be requested when an instrument is ready for an assay. FIG. 13 illustrates some XML code describing a container that follows the parameters of FIG. 12. As in FIG. 12, the data illustrated in FIG. 13 is cut from a larger example, and is not meant to represent a complete container description, or proper XML formatting. Starting at section 1305, the container's descriptive information is given, including name, ID, owner, and comment. These descriptors correspond to the descriptor parameters given in section 1210 of FIG. 12. Sections 1310 and 1315 describe data chosen based on parameters received in the XML data of FIG. 12. In section 1310, which corresponds to the parameters described in section 1230 of FIG. 12, the container data describes itself as utilizing a heat seal, and utilizes one of the values described in section 1230. In section 1315, a scheduling preference number is given, which is taken from the range described in section 1235 of FIG. 12.

Section 1320 gives one example of a set of assay data. This data describes a particular well of the container (A1), gives a sample name and tracking ID, and describes the assay protocol used and how the results should be stored. Unlike the data described in sections 1305, 1310, and 1315, this data does not correspond to parameters explicitly given by any section of FIG. 12. Instead, the data given was created by the use of an instantiation of the class described in section 1225 of FIG. 12. Thus it is illustrated how a more complex piece of container or assay data may be created by a class described in parameter XML data.

FIG. 14 illustrates XML data describing manual control parameters for an instrument, in this case an electrophoresis instrument. Data such as in FIG. 14 will typically be obtained by a client after a manual commands request to an instrument type server. Then, as discussed above, command strings can be sent to an instrument using the Framework Instrument Interface. As in FIGS. 12 and 13, the data included in FIG. 14 is cut from a larger example and is not meant to represent a complete set of manual control parameters, nor strict XML code.

At section 1405, and indication of a group of commands is given; in this example, the group is electrophoresis commands. In one embodiment, a given instrument may have more than one group of commands, such as commands describing an over used to heat a sample and a syringe used to deliver the same to and from a well. Sections 1410-1425 describe parts of the XML data for a particular command. In section 1410, the name of the command is given; in this case it is to set the power supply. In section 1415, a command string is given. This, along with the parameter given in section 1425, is what a client would send an instrument in order to manually turn the electrophoresis power on or off. Next, at section 1420, a comment describing the nature of the command is given. The use of the name and comment indicators is advantageous if a client wishes to provide a user interface to the laboratory technician that is setting up the instrument. Then in section 1425, the parameters are given for the command. Here, they are a list consisting of on and off. In other embodiments, a list of different lengths or utilizing non-string values can be used.

Two other types of commands are illustrated in contrast to the one described above. In section 1445, a command is illustrated for an electrophoresis voltage setting. Rather than provide a list of discrete settings, the command parameters in section 1445 describe a floating-point value in the range 0.0-15.0. Thus, a client can submit a command request giving any value in this range and trust that the instrument will accept the command. In section 1460 a command is illustrated allowing a client to request a reading of the electrophoresis voltage from an instrument. As this is a request for a value, no parameters are listed and the client needs only be made aware of the command string.

As with the other XML data examples given, the example of FIG. 14 demonstrates the flexibility of the system in that multiple types of instrument parameters can be described and delivered to a client, while giving enough information that a simple command can be sent back to the instrument to implement the client's needs.

Figure 15:
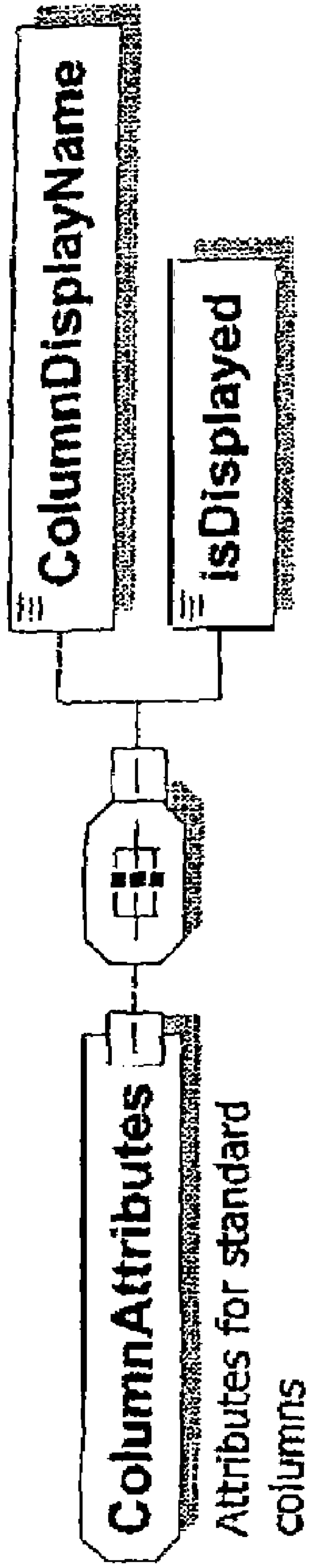
FIG. 15 illustrates an example XML schema describing the structure of data describing container parameters.
Figure 16:
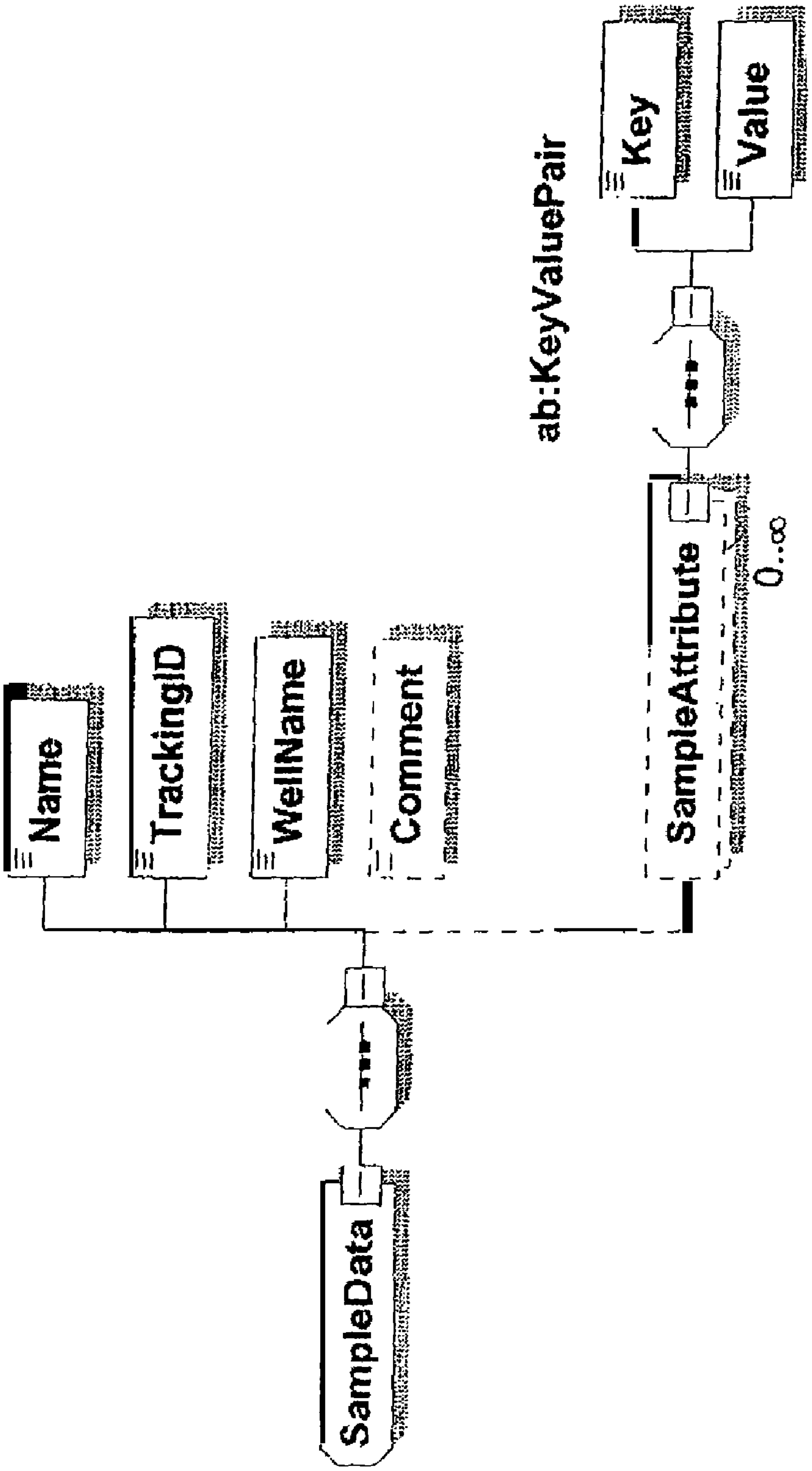
FIG. 16 illustrates an example XML schema describing the structure of data describing container assay parameters.
Figure 17:
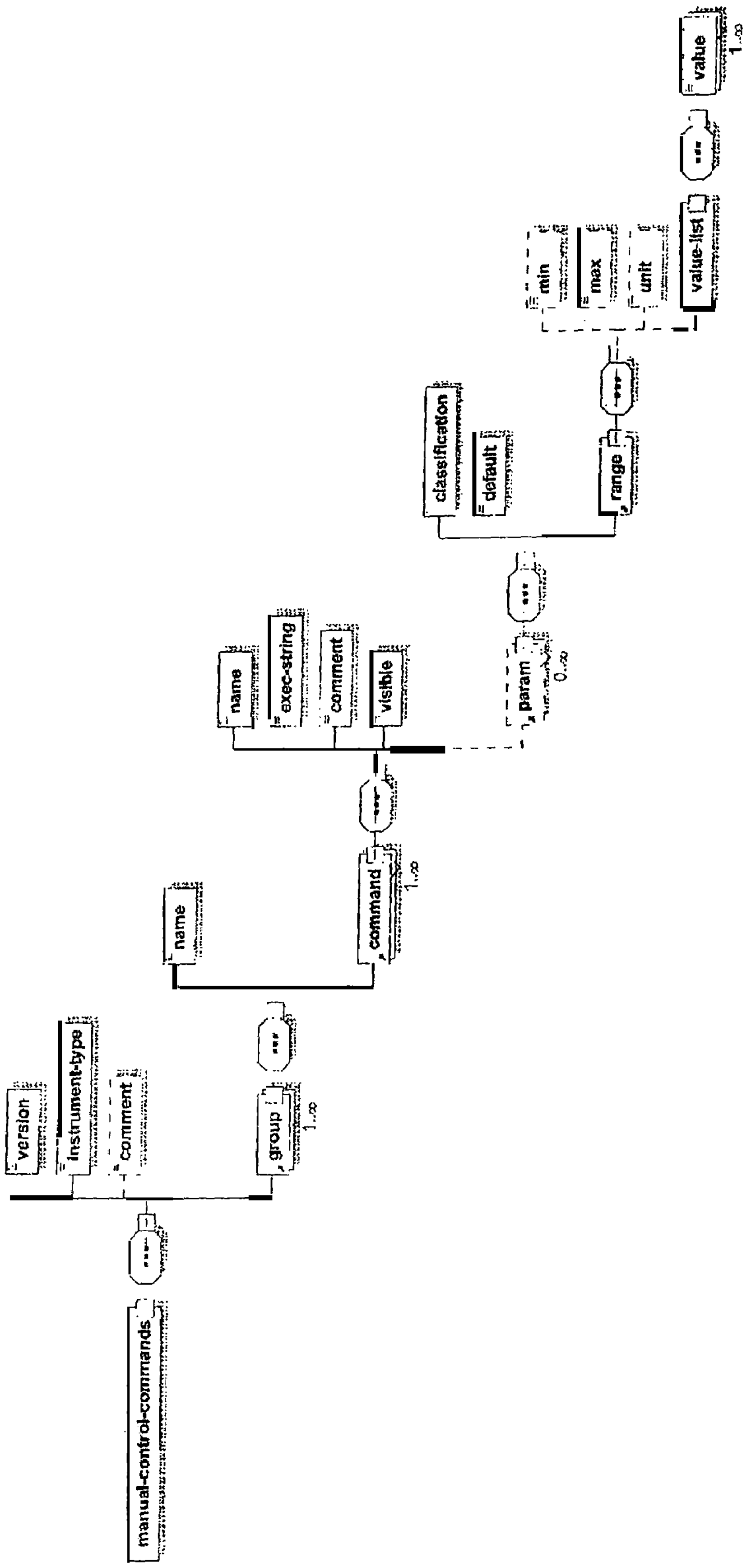
FIG. 17 illustrates and example XML schema describing the structure of data describing manual control parameters.

FIGS. 15, 16 and 17 illustrate, in one embodiment of the invention, XML schemas defining the structure of XML data used to discover instrument parameters. FIG. 15 illustrates a schema describing samples and container parameters. The schema illustrated in FIG. 15 describes the structure of the XML data example illustrated in FIG. 12. FIG. 16 illustrates a schema for describing parameters for an assay and containers for that assay. The schema illustrated in FIG. 16 describes the structure of the XML data example illustrated in FIG. 13. FIG. 17 illustrates a schema describing manual control parameters for an instrument type. The schema illustrated in FIG. 17 describes the structure of the XML data example illustrated in FIG. 14. It should be understood that certain variations and modifications of this invention will suggest themselves to one of ordinary skill in the art. The scope of the present invention is not to be limited by the illustrations or the foregoing descriptions thereof.

Figure 18:
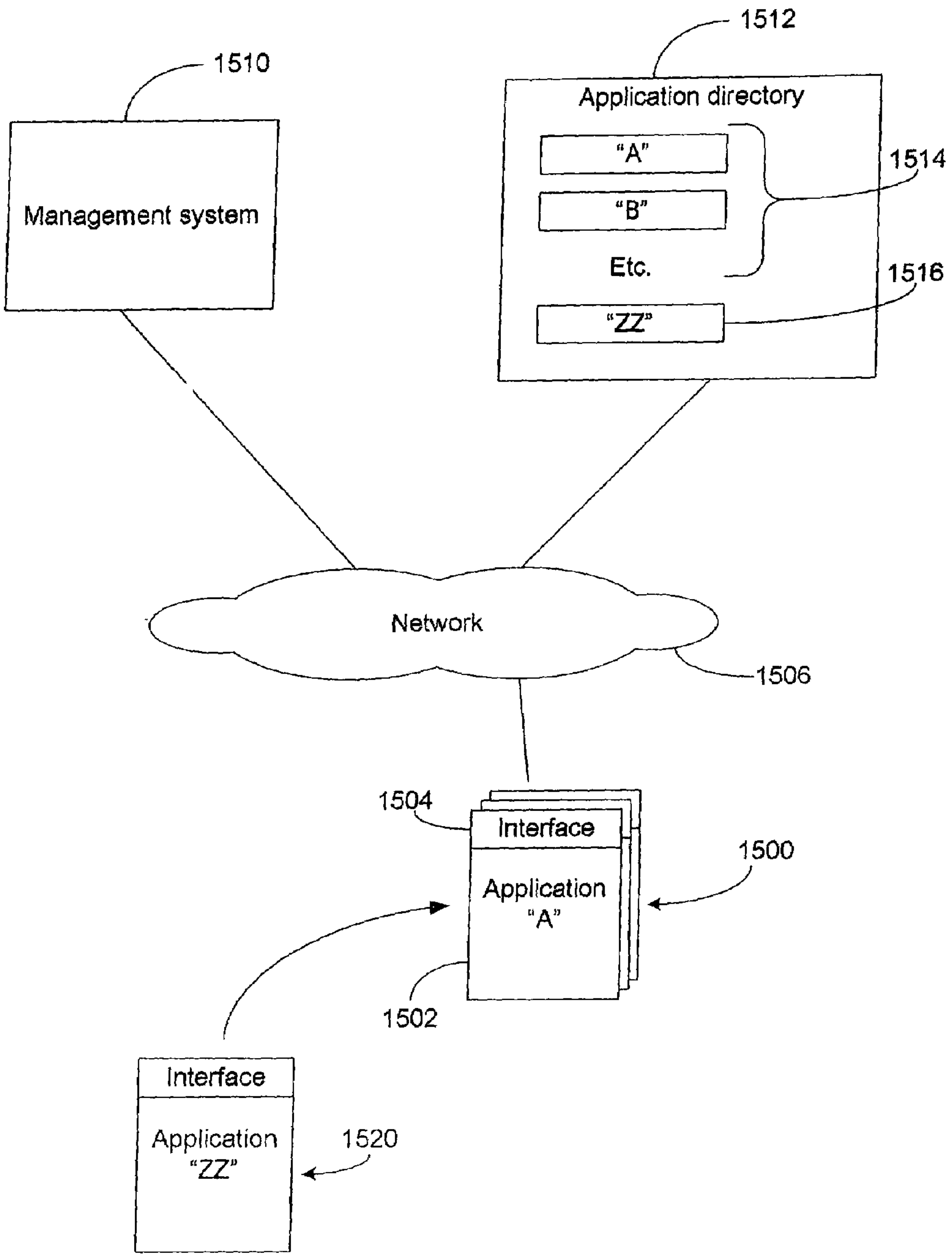
FIG. 18 illustrates an integration of an exemplary application into an existing system in a manner similar to that for instruments.

It will be appreciated that the concept of integrating an instrument into the laboratory system framework may be extended to include various software applications as well. FIG. 18 illustrates an exemplary system where a new application 1520 is being added. The system may already have one or more applications 1500 integrated. Similar to the integration of instruments as described above, the applications 1500 may comprise application portions 1502 that interact with the system via interfaces 1504. In certain embodiments, the interaction with the rest of the system is performed via a network 1506.

Such integration and operation of the applications 1500 may be facilitated by an application directory 1512 that comprises information 1514 about the applications' 1500. Such an information structure may be similar to that of instruments described above. In certain embodiments, the information about the applications may be stored in a same directory as that of the instruments. In certain embodiments, the information about the applications may be stored separately from that of the instruments. It will be appreciated that the information about the application and/or the instruments may be stored in one or more directories in any combination without departing from the spirit of the present teachings.

FIG. 18 further illustrates that when the new application ("ZZ") 1520 is added to the system, information 1516 about the application 1520 is added to the directory 1512. Such addition of the information in the directory 1512 may be performed in a similar manner as that of the instruments described above. Once the application 1520 is integrated into the system and recognized by the system, it could be utilized in a variety of integrated manner to facilitated the biological assay process in a manner similar to that of the integrated instruments.

It will be appreciated that a biological laboratory configured in one or more of the foregoing configurations provide many advantages for processing biological samples and analyzing data gathered therefrom. Such advantages can be particularly appreciated when the number of instruments/applications and the samples are relatively large. In such a situation, a user attempting to coordinate a large number of biological assays may not utilize the resources of the laboratory in an efficient or convenient manner.

In one aspect, the integrated framework disclosed herein allows a user to plan an assay at a high-level of abstraction, and let the framework and its various systems handle and execute the various details. For example, the user may instruct the management system to perform a particular protocol on a particular sample. At this level of abstraction, the user may issue such instruction without having to be concerned with the details of how such protocol will be performed on the sample.

In one example of such an instruction involving high-level instrument protocols, a given sample is instructed to undergo a sample multiplying process followed by an electrophoresis measurement. This exemplary high-level instruction can then be implemented when the identified sample is retrieved from its storage location and moved to an available thermalcycler. The multiplication of the sample can then be carried out in the selected thermalcycler. The multiplied samples can then be processed by one or more selected electrophoresis instruments. Information that allow implementation of the high-level instruction may include details such as the location of the sample, the availability and condition of the selected thermalcycler and the electrophoresis instruments. As previously described, such details may be stored in the instrument and/or sample directory(ies).

In one aspect, such high-level abstraction concept includes a selection of instruments and/or software applications as needed. Such selection of the instruments and/or applications allow the laboratory system to utilize the resources in a more efficient manner by not tying up resources to a particular set of protocols. This concept of utilizing the instrument/application resources in an advantageously as-needed basis (as compared to the "committed resources" manner) is illustrated in FIGS. 19A-B.

Figure 19A:
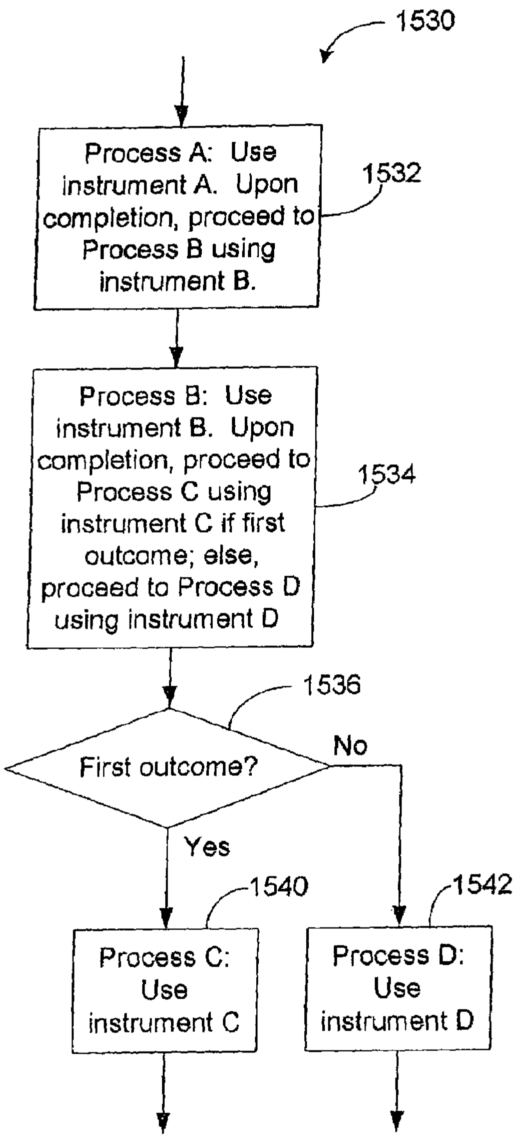
FIGS. 19A and B illustrate possible methods of allocating resources during a biological assay process.
Figure 19B:
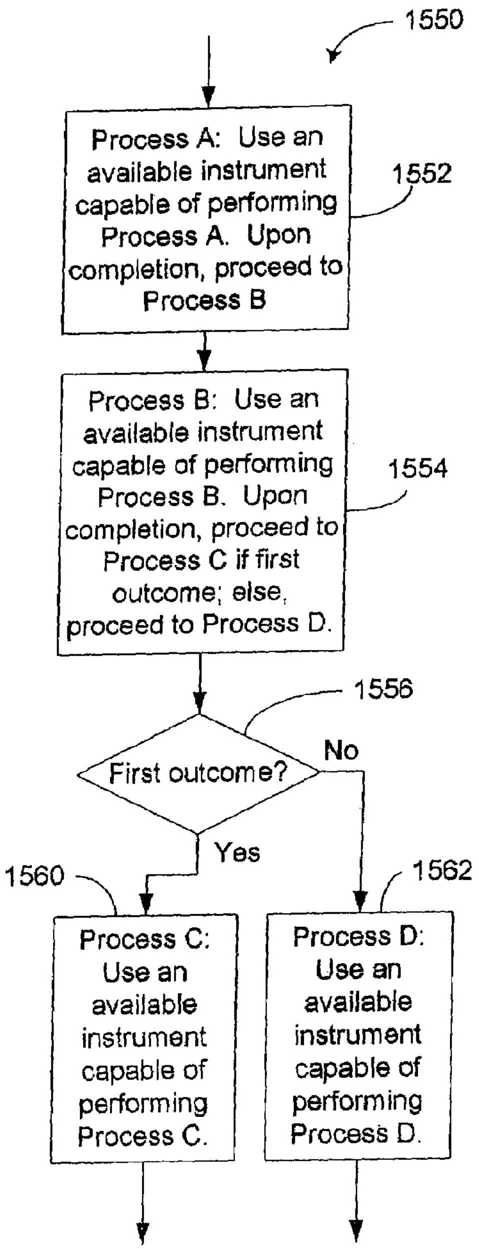
FIG. 19C illustrates a possible embodiment of a hardware sharing layer that allows shared access to a hardware having a limited number of access ports.

FIG. 19A illustrates a portion of one possible assay process 1530 that may be implemented in the aforementioned "committed" manner. The exemplary process 1530 is prescribed such that to perform exemplary processes A, B, C, and D, corresponding instruments A, B, C, and D are committed during the duration of the process 1530. Specifically, in step 1532, the process 1530 uses instrument A to perform process A. Upon completion of process A, the assay process 1530 proceeds to step 1534, where instrument B is utilized to perform process B. The exemplary process B may have two or more possible outcomes - a first outcome and other outcome(s).

As seen in FIG. 19A, the assay process 1530 is instructed to utilize instrument C if process B's outcome is a first outcome. Otherwise, the assay process 1530 is instructed to utilize instrument D. Such a decision is made in a decision step 1536. If the answer is a "Yes," the outcome of B is a first outcome, and the assay process 1530 proceeds to step 1540 where instrument C is used to perform process C. If the answer is a "No," the outcome of B is the other outcome, and the assay process 1530 proceeds to step 1542 where instrument D is used to perform process D.

In certain embodiments, a similar assay may be performed in a different manner, wherein the resources are not pre-assigned as in the process 1530 of FIG. 19A. The resources are instead assigned "just in time" to perform the desired functions of the assay. As shown in FIG. 19B, an exemplary assay process 1550, instead of using a predetermined instrument in step 1552, uses an available instrument that is capable of performing process A. Upon completion of process A, the assay process 1550 proceeds to step 1554, where an available instrument capable of performing process B is used to perform process B.

As seen in FIG. 19B, the assay process 1550 is instructed to perform process C if process B's outcome is a first outcome. Otherwise, the assay process 1550 is instructed to perform process D. Such a decision is made in a decision step 1556. If the answer is a "Yes," the outcome of B is a first outcome, and the assay process 1550 proceeds to step 1560 where an available capable instrument is used to perform process C. If the answer is a "No," the outcome of B is the other outcome, and the assay process 1550 proceeds to step 1562 where an available capable instrument is used to perform process D.

One can see that by committing an instrument "just in time" as need arises, the overall efficiency of resources utilization can be improved. It will be appreciated that such an assignment of resources may be facilitated and used more effectively when a laboratory includes a relatively large number instruments. It will also be appreciated that the depiction of the exemplary processes 1530 and 1550 in FIGS. 19A-B are in no way intended to limit the manner in which resources are utilized. That is, an assay process may utilize any combination of these two exemplary resource-allocation schemes without departing from the spirit of the present teachings.

In certain embodiments, the concepts of laboratory-universal recognition and support of the various instruments and applications, provided by the common architecture of the present teachings, are extended to include various files that store various information about samples being processed. Such files may include raw data files that are generated by the analytical instruments. The files may also include processed data files that result from processing of the raw data files by one or more applications.

Preferably, such sample-related files (and any other related files) are formatted to store arbitrary information such that a user accessing the files at a high-level does not need to worry about the details of file-specific details. Such file-specific details may be delegated to an entity analogous to the instrument directory described herein. Thus when the user wishes certain data or information to be stored, the implementation of such a storing process is carried out in a manner similar in spirit to the user-instrument interaction. Similarly, retrieval of data or information may be carried out in a similar manner.

Also preferably, the sample-related files are configured so as to be expandable to accommodate possible changes in the volume of information being stored. For example, a given instrument may be upgraded, and the resulting raw data may be of a greater resolution and encompass a greater dynamic range. Preferably, such changes in the raw data size are accommodated by the sample-related files. Such files that accommodate the changes in the exemplary data are also preferably backward-compatible, such that existing software applications can access the "changed" data file in a transparent manner. Such a functionality may be achieved, for example, by placing a header information for the data file, wherein the header includes the format of the data therein. Such an information may stored away from the data file itself in the form of an updated instrument information in the instrument directory.

In various embodiments, the various components of the LIMS system may be configured to permit access by multiple users. One means by which this may be accomplished is through the implementation of a hardware sharing layer that provides for simultaneous access. Thus for a selected instrument, multiple service tools and/or data collection software applications may access the resources of the instrument in a substantially transparent manner.

In one aspect, the hardware sharing layer may be used for the purposes of quality control, diagnostic, and checkout functions while simultaneously permitting user access or normal instrument runtime operations. Additionally, the hardware sharing layer may be used for the purposes of research and development on prototype instruments for which data collection software may not yet exist allowing a convenient means by which multiple users may access the resources of the instrument. An additional benefit of the hardware sharing layer is to provide a means to encapsulate knowledge of instrument-specific hardware interactions, allowing hardware developers to work to a single protocol for instrument communications.

In various embodiments, implementation of the hardware sharing layer (HSL) provides for convenient instrument accessibility and possesses the following characteristics: (a) The HSL allows simultaneous connection to a physical instrument by multiple clients. (B) The HSL may be used by Java and non-Java clients and further provide for web-browser based connectivity if desired. (c) The HSL may permit a selected client to be informed of the activity of other clients connected to a selected instrument or class of instruments. (d) The HSL may provide a deliverable communications implementation in the absence of the full data collection infrastructure. (e) The HSL is desirably configured to be substantially independent of underlying communications layers, instrument specific implementations, and third-party technologies to provide for improved compatibility and flexibility. Additionally, the hardware sharing layer may provide a means to configure resource limited communication paths such as firewire or serial connections to allow for shared resource access by implementation of a HSL front-end.

Figure 19C:
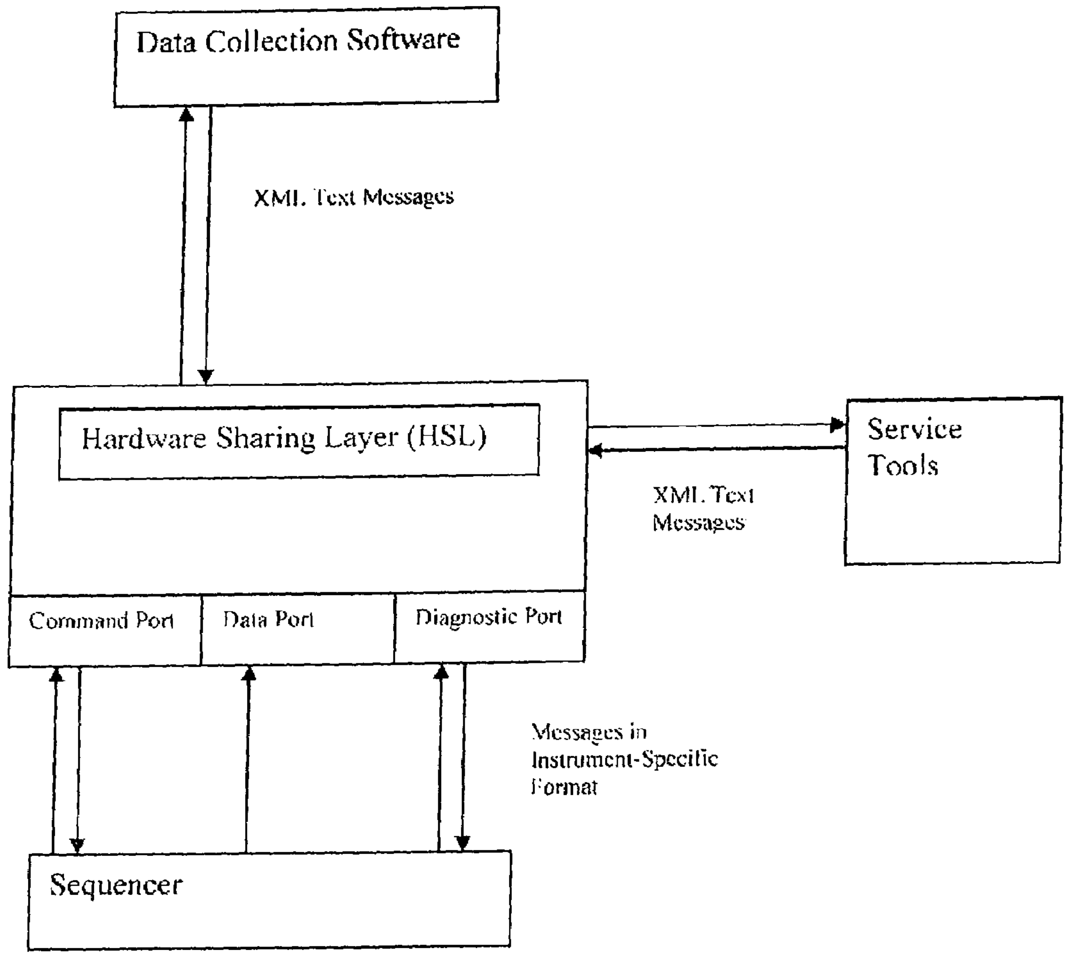

FIG. 19C illustrates one embodiment of a hardware sharing layer architecture for a sequencer that may be used in connection with the system and methods of the present teachings. In one aspect, hardware and components may be viewed as a collection of "channels". For example, the various biological instruments such as gene sequencers may communicate through a multiplicity of TCP ports. Typically, these ports may include a command, data, and diagnostic port with each port having a channel through which messages may be addressed. Each message may comprise an envelope with a channel address and a "payload communication" that may be instrument dependent. For sequencers, the payload may comprise a SCPI command. For an instrument which is controlled via a traditional DLL, the sharing layer may be responsible for translating the payload into the necessary DLL function calls.

In general, messages may be transferred between clients and the HSL using conventional TCP sockets or an equivalent communications protocol means. The use of TCP sockets is well understood and represents a nearly universal mechanism that is relatively easy to implement for many different programming languages and operating systems.

The system comprises an HSL server and one or more channel plug-ins which conform to a standard "Channel" interface understood by the server. In various embodiments, channel plug-ins may choose to implement some domain knowledge of the particular channels they manage, but the server itself need not necessarily maintain such knowledge. As an example, channels for the command and diagnostic ports on an exemplary sequencer may be aware that incoming data is newline delimited, and may use this knowledge in deciding when to bundle up a set of incoming bytes for relay to the client.

In various embodiments, messages transmitted through the HSL may be characterized by a "Type" attribute which defines the purpose of the message, and a "Channel" attribute which specifies the source or destination of the message. For messages that are intended to be transmitted to or from the HSL layer itself, such as a request for a channel enumeration, the Channel attribute may be designated as "HSL". Other channels may be instrument-specific. The content of the message is generally considered to be message-type dependent. The following table below outlines some exemplary message types, and is followed by sample XML-like message strings that may be used in implementation.

| Message | Direction | Message 'Type' Attribute | Notes |
|---|---|---|---|
| Close Connection | To HSL | CloseConnection | Send just before closing client TCP port. |
| Subscribe To Channel | To HSL | SubscribeToChannel | Client will receive all output from this channel (see "Message" below) |
| Send Message To Channel | To HSL | ToChannel | Message content is channel-specific |
| Message From Channel | To Client | FromChannel | Channel has said something. All subscribers get the message. |
| Lock Channel | To HSL | LockChannel | Allow no other clients to send to this channel. |
| UnLock Channel | To Client | UnLockChannel | |
| Snoop Sends To Channel | To HSL | SnoopChannel | Listen to all Sends by other clients. |
| Snooped Message | To Client | SnoopedSend | Message sent from another client to the channel. |
| UnSnoop Sends To Channel | To Client | UnSnoopChannel | Quit snooping |
| Get Channel Lock State | To HSL | GetLockState | Does any client have a lock? |
| Channel Lock State | To Client | LockState | Response to the previous "get" |
| Command Failed | To Client | CommandFailure | Example: Attempt to send to a non-existent channel. |
| Get Channel Enumeration | To HSL | GetChannelEnumeration | |
| Channel Enumeration | To Client | ChannelEnumeration | |
| Get Connection Enumeration | To HSL | GetConnectionEnumeration | Get a list of all connections |
| Connection Enumeration | To Client | ConnectionEnumeration | |
| Connection Opened | To Client | ConnectionOpened | All clients will be notified when any connection is opened or closed. |
| Connection Closed | To Client | ConnectionClosed | |
| Channel Locked | To Client | ChannelLocked | All clients will be notified when any locks are acquired or released. |
| Channel UnLocked | To Client | ChannelUnLocked | All clients will be notified when any locks are acquired or released. |
| Channel has gone | To | ChannelOffline | e.g. TCP connection has been |

-continued

| Message | Direction | Message 'Type' Attribute | Notes |
|---|---|---|---|
| off-line | Client | | broken. |
| Channel has come on-line | To Client | ChannelOnline | e.g. TCP connection has been re-established. |

Additional details of various messages:

SubscribeToChannel (Client->HSL)

Output from the given channel may be routed to this client. Clients may subscribe to multiple channels on a single TCP port and then parse the "Channel" attribute on incoming messages, or may wish to open a different port for each channel.

Channel names may be fixed for each instrument type and are generally not expected to change. The GetChannelEnumeration (see below) message may be used to verify the channel names.

EXAMPLE

```
<HSLMsg Type="SubscribeToChannel" Channel="CmdPort">
</HSLMsg>
```

ToChannel (Client->HSL), default ASCII format example

This message may be used to send information from the client to a channel. The default content format may be ASCII (bytes with numeric values between 0 and 127). In general, bytes between the <Content> </Content> tags will be routed to the channel. For example, a message composed in a text editor with the <Channel> attribute on a separate line from the first line of content will contain a leading newline (which is editor and operating-system dependent!) preceding any other content routed to the channel.

In the following example for a sequencer, note that there is a CRLF following the SCPI message content, since this may be required by the instrument.

EXAMPLE

```
<HSLMsg Type="ToChannel" Channel="DiagPort">
<Content>
DIAG:MST Off
</Content>
</HSLMsg>
```

FromChannel (HSL->Client)

The following may be the response that would be sent by a sequencer diagnostic port to the previous example

EXAMPLE

```
</HSLMsg><HSLMsg Type="FromChannel" Channel="DiagPort">
<Content>OK DIAG:MST OFF
</Content></HSLMsg>
```

GetChannelEnumeration (Client->HSL)

This message may ask the HSL to send a list of all Channels.

EXAMPLE

```
<HSLMsg Type="GetChannelEnumeration" Channel="HSL">
</HSLMsg>
```

ChannelEnumeration (HSL->Client)

This message may be returned in response to the GetChannelEnumeration message. The individual channel names may be delimited by newlines. The response shown here is what may be expected for a sequencer.

EXAMPLE

```
<HSLMsg Type="ChannelEnumeration" Channel="HSL">
<Content>
DiagPort
DataPort
CmdPort
</Content></HSLMsg>
```

CommandFailure (HSL->Client)

This message may indicate that the previous command sent by the client could not be parsed successfully, for example a tag or attribute was misspelled, or an invalid Channel name was provide.

EXAMPLE

```
<HSLMsg Type="CommandFailure" Channel="HSL">
<Content>Invalid channel</Content></HSLMsg>
```

ChannelOffline (HSL->Client)

This message may be sent if a channel goes down. For a sequencer, this typically means the TCP connection has been lost.

```
<HSLMsg Type="ChannelOffline" Channel="DiagPort">
</HSLMsg>
```

ChannelOnline (HSL->Client)

This message may be sent when a channel comes up. For a sequencer, this typically means the TCP connection has been re-established when the instrument has been powered-up.

<HSLMsg Type="ChannelOnline" Channel="DiagPort">
</HSLMsg>.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A control and communications system for a laboratory, the system comprising:

a client component configured to control or monitor the operation of at least one biological analyzer;

at least one analyzer component associated with the at least one biological analyzer configured to receive instructions from the client component and translate the instructions into commands capable of inducing the associated biological analyzer to conduct an analysis and provide data indicative of the analysis;

at least one directory configured to provide information to the client component as to the logical location and parameters of said at least one analyzer component such that the client component is able to control or monitor the at least one biological analyzer by referencing the information provided by the at least one directory to induce the at least one biological analyzer to conduct the analysis; and a messaging service configured to communicate with the at least one analyzer component and the client component such that a new biological analyzer can be configured to be included in the laboratory by associating at least one of the analyzer components with said new biological analyzer and updating the at least one directory with information as to the logical location of the analyzer component allowing the client component to control or monitor the new biological analyzer using the parameters provided by the at least one directory.

2. The system of claim 1, wherein the biological analyzer is a biological data analyzer.

3. The system of claim 2, wherein the biological data analyzer comprises an application configured to analyze biological sample constituents selected from the group consisting of: DNA, RNA or protein.

4. The system of claim 1, wherein the biological analyzer comprises an instrument configured to perform at least one of the functions selected from the group consisting of: single nucleotide polymorphism analysis and structural analysis.

5. The system of claim 1, wherein the at least one biological analyzer comprises at least one instrument selected from the group consisting of: thermal cyclers, sequence detection instruments, and electrophoresis instruments.

6. The system of claim 1, wherein the at least one biological analyzer comprises at least one robotic instrument configured to identify and physically manipulate at least one biological sample.

7. The system of claim 1, wherein the at least one directory is configured to respond to requests by the client component for information about a requested biological analyzer providing the logical location of the analyzer component associated with the requested biological analyzer thereby providing a mechanism for the client component to communicate with the biological analyzer via the messaging service.

8. The system of claim 1, further comprising at least one server component configured to provide data to the at least one directory that describes the parameters associated with a particular biological analyzer.

9. The system of claim 8, wherein the at least one directory is configured to respond to requests by the client component for information about a requested server component providing the logical location of the server component thereby providing a mechanism for the client to communicate with the server via the messaging service.

10. The system of claim 1, wherein the client component controls and monitors the operation of the one or more biological analyzers using a generic instruction set translated into appropriate biological analyzer-specific commands by the analyzer component.

11. The system of claim 1, wherein the client component communicates with the one or more biological analyzers using a generic communication set translated into appropriate biological analyzer-specific communications by the at least one directory.

12. The system of claim 1, wherein the information provided by the at least one directory includes information identifying one or more of the following: biological analyzer type, biological analyzer groups, biological analyzer serial numbers, available biological analyzers and physical localities for biological analyzers; and the at least one directory provides at least a portion of the information to the client component as requested allowing available biological analyzers in the laboratory to be identified.

13. The system of claim 1, wherein:

the information contained in the at least one directory identifies each biological analyzer and includes a topic list under which messages are published by the at least one analyzer component associated with each biological analyzer;

the messaging service provides a mechanism for the client component to register and receive messages published by the analyzer components that correspond to topics in the topic list selected by the client component; and the messaging service responds to publication requests for messages under an associated topic from an analyzer component sending the message to each of the at least one client components that registered to receive messages for that topic.

14. The system of claim 1, wherein the directory is implemented using the Java Naming and Directory Interface and the messaging service is implemented using a Java Messaging service.

15. The system of claim 1, wherein each analyzer component provides for at least one of the following functionalities: control of the biological analyzer, receiving biological analyzer status information, receiving biological analyzer history information, transmitting information to the biological analyzer and receiving information from the biological analyzer.

16. The system of claim 1, wherein each analyzer component comprises software modules, including:

a state model module configured to maintain a state of the biological analyzer within a corresponding state model, wherein the client component instructions cause transitions within the state model; and a translation module, which translates instructions received from the client component implementing commands for effectuating transitions within the state model and translates these instructions into commands recognized by the biological analyzer.

17. The system of claim 1, wherein the parameters of said at least one biological analyzer comprise at least one of the following: container parameters, assay parameters, and information relating to manual control parameters for a selected biological analyzer.

18. The system of claim 1, wherein the parameters of said at least one analyzer component comprise XML instructions.

19. The system of claim 1, wherein the at least one directory is configured to include information regarding available software applications and wherein new software applications may be integrated into the system by updating the at least one directory with appropriate information regarding the new software application.

20. The system of claim 1, wherein a hardware sharing layer provides a mechanism for multiple or simultaneous connection to at least one biological analyzer by multiple client components.

21. The system of claim 20, wherein the hardware sharing layer supports Java and non-Java based client components.

22. The system of claim 20, wherein the hardware sharing layer supports web-browser based connectivity.

23. The system of claim 20, wherein the hardware sharing layer allows a selected client component to be informed of other client component activity.

24. The system of claim 20, wherein the hardware sharing layer improves flexibility by operating substantially independently of underlying communications layers and biological analyzer specific implementations.

25. A method for controlling the operation of a laboratory, the method comprising:

associating at least one analyzer component with at least one biological analyzer wherein the at least one analyzer component translates received instructions into commands recognized by the at least one biological analyzer directing the at least one biological analyzer to conduct analyses and provide data indicative of the analyses;

maintaining a directory providing information as to the logical location and parameters of each analyzer component within the laboratory allowing a client component to access the at least one biological analyzer and implement at least one process to direct the at least one biological analyzer to conduct the analyses; and adding a new biological analyzer to the laboratory by associating at least one analyzer component with the newly added biological analyzer and updating the directory as to the logical location of the biological analyzer such that the new biological analyzer is discoverable and accessible by the client component providing a mechanism to implement at least one process to direct the new biological analyzer to conduct analyses.

26. The method of claim 25, further comprising maintaining in the directory at least one group of instructions for each of the biological analyzers within the laboratory such that the client components can access the directory and determine which of the at least one group of instructions are implemented by each analyzer component allowing the client component to access a biological analyzer implementing a selected process.

27. The method of claim 26, wherein each biological analyzer accessed during the implementation of the selected process is assigned to the selected process upon its onset.

28. The method of claim 26, wherein each biological analyzer accessed during the implementation of the selected process is selected from one or more of biological analyzers capable of conducting the analysis.

29. The method of claim 28, wherein resource utilization is improved by selection of the biological analyzer just prior to the access of the biological analyzer.

30. The method of claim 25, further comprising transmitting signals between the at least one client component and the at least one analyzer component using a generic list of instructions that are translated by the analyzer component into specific commands to control the biological analyzer.

31. The method of claim 30, wherein the analyzer component translation is provided by a translation protocol used to translate the generic list of instructions into specific commands that the biological analyzer is programmed to implement.

32. The method of claim 25, wherein the biological analyzer is instructed to analyze DNA, RNA or protein constituents of biological samples.

33. The method of claim 25, wherein the biological analyzer is instructed to perform single nucleotide polymorphism analysis or structural analysis.

34. The method of claim 25, further comprising maintaining at least one set of biological type information for each biological analyzer such that the client component can determine biological analyzer type parameters by accessing a server that maintains the biological type information.

35. The method of claim 25, further comprising transmitting a signal to the client component indicating those biological analyzers available in the laboratory.

36. The method of 25, further comprising:

maintaining in the directory a list of topics under which messages are published by the at least one analyzer component associated with each biological analyzer;

registering the at least one client component with a messaging service such that the client component receives messages published by at least one analyzer component corresponding to topics selected by the client component; and transmitting messages for each topic to the messaging service so that the messages are disseminated to client components registered to receive messages under selected topics.

37. The method of claim 25, further comprising responding to a request by the client component for information about a requested biological analyzer or biological analyzer type with a response containing at least one logical location for at least one analyzer component associated with the requested biological analyzer or with a logical location for a server containing biological analyzer type information for the requested biological analyzer type so that the client component can access the requested biological analyzer or biological analyzer type information through a messaging service.

38. The method of claim 37, wherein responding to the request allows management of the at least one biological analyzers by the client component at a high-level without requiring the client component to posses specific details of the biological analyzer wherein such details are provided by the directory.

39. The method of claim 25, wherein the directory is configured to include information identifying at least one software application configured for use in the laboratory and wherein additional new software applications can be integrated within the laboratory by updating the directory to include information about the new software application.

* * * * *

UNITED STATES PATENT AND TRADEMARK OFFICE

CERTIFICATE OF CORRECTION

PATENT NO. : 7,379,823 B2
APPLICATION NO. : 11/023329
DATED : May 27, 2008
INVENTOR(S) : Yung et al.

It is certified that error appears in the above-identified patent and that said Letters Patent is hereby corrected as shown below:

Title Page item 56, Page 2, Column 2 (Other Publications)

Line 10, delete “10,455,263” and insert -- 10/455,263. --, therefor.

(In Drawings) Sheet 11 of 23 (Reference Numeral 1003) (FIG. 10)

Line 1, delete “LIMSA” and insert -- LIMS --, therefor.

Sheet 16 of 23 (FIG. 13)

Line 31, delete “Protocoll” and insert -- Protocol --, therefor.

Column 4

Line 19, delete “a” and insert -- an --, therefor.

Column 9

Line 29, delete “system,.this” and insert -- system, this --, therefor.

Column 12

Line 16, delete “examples” and insert -- example --, therefor.

Column 17

Line 41, delete “a” and insert -- an --, therefor.

Column 20

Line 26 (Approx.), delete “a” and insert -- an --, therefor.

Column 22

Line 29, delete “facilitated” and insert -- facilitate --, therefor.

UNITED STATES PATENT AND TRADEMARK OFFICE

CERTIFICATE OF CORRECTION

PATENT NO. : 7,379,823 B2
APPLICATION NO. : 11/023329
DATED : May 27, 2008
INVENTOR(S) : Yung et al.

It is certified that error appears in the above-identified patent and that said Letters Patent is hereby corrected as shown below:

Column 24

Line 58, delete "(B)" and insert -- (b) --, therefor.

Signed and Sealed this

Twenty-fifth Day of August, 2009

David J. Kappos

David J. Kappos
*Director of the United States Patent and Trademark Office*